US009364239B2

(12) United States Patent
Malkowski

(10) Patent No.: US 9,364,239 B2
(45) Date of Patent: Jun. 14, 2016

(54) JAW CLOSURE MECHANISM FOR A SURGICAL CLIP APPLIER

(71) Applicant: Covidien LP, Mansfield, MA (US)

(72) Inventor: Jaroslaw T. Malkowski, Trumbull, CT (US)

(73) Assignee: Covidien LP, Mansfield, MA (US)

( * ) Notice: Subject to any disclaimer, the term of this patent is extended or adjusted under 35 U.S.C. 154(b) by 388 days.

(21) Appl. No.: 13/674,130

(22) Filed: Nov. 12, 2012

(65) Prior Publication Data

US 2013/0310849 A1  Nov. 21, 2013

Related U.S. Application Data

(60) Provisional application No. 61/577,130, filed on Dec. 19, 2011.

(51) Int. Cl.
*A61B 17/10*  (2006.01)
*A61B 17/128*  (2006.01)
*A61B 17/29*  (2006.01)

(52) U.S. Cl.
CPC .......... *A61B 17/128* (2013.01); *A61B 17/1285* (2013.01); *A61B 2017/2911* (2013.01); *A61B 2017/2937* (2013.01)

(58) Field of Classification Search
CPC ............. A61B 17/128; A61B 17/1285; A61B 17/2804; A61B 17/30; A61B 2017/2911; A61B 2017/2937
USPC .................................. 606/142, 205, 207, 208
See application file for complete search history.

(56) References Cited

U.S. PATENT DOCUMENTS

| 3,120,230 A | 2/1964 | Skold |
| 3,363,628 A | 1/1968 | Wood |
| 3,638,847 A | 2/1972 | Noiles et al. |
| 3,867,944 A | 2/1975 | Samuels |

(Continued)

FOREIGN PATENT DOCUMENTS

| AU | 2010200641 A1 | 10/2010 |
| CN | 100571640 C | 12/2009 |

(Continued)

OTHER PUBLICATIONS

Extended European Search Report corresponding to EP 10 25 2112.7, completed Jul. 29, 2014 and mailed Aug. 5, 2014; (8 pp).

(Continued)

*Primary Examiner* — Corrine McDermott
*Assistant Examiner* — Sarah Simpson

(57) ABSTRACT

A jaw closure mechanism for use in a surgical clip applier having first and second jaws movable relative to one another between a spaced-apart position and an approximated position to form a surgical clip about tissue. The jaw closure mechanism includes first and second eccentric wheels rotatably coupled to the respective first and second jaws. Each of the wheels includes a center and a pivot point that is offset relative to the center. A cable is disposed about each of the wheels. The cable is engaged to the first wheel at a first engagement point and to the second wheel at a second engagement point such that, upon application of a drive force to the cable, the wheels are rotated and displaced relative to the respective jaws from a first position to a second position to urge the jaws from the spaced-apart position to the approximated position.

16 Claims, 4 Drawing Sheets

(56) References Cited

U.S. PATENT DOCUMENTS

| | | |
|---|---|---|
| 4,242,902 A | 1/1981 | Green |
| 4,296,751 A | 10/1981 | Blake, III et al. |
| 4,372,316 A | 2/1983 | Blake, III et al. |
| 4,408,603 A | 10/1983 | Blake, III et al. |
| 4,412,539 A | 11/1983 | Jarvik |
| 4,480,640 A | 11/1984 | Becht |
| 4,480,641 A | 11/1984 | Failla et al. |
| 4,487,204 A | 12/1984 | Hrouda |
| 4,487,205 A | 12/1984 | Di Giovanni et al. |
| 4,491,133 A | 1/1985 | Menges et al. |
| 4,492,232 A | 1/1985 | Green |
| 4,498,476 A | 2/1985 | Cerwin et al. |
| 4,500,024 A | 2/1985 | DiGiovanni et al. |
| 4,509,518 A | 4/1985 | McGarry et al. |
| 4,512,345 A | 4/1985 | Green |
| 4,522,207 A | 6/1985 | Klieman et al. |
| 4,532,925 A | 8/1985 | Blake, III |
| 4,534,351 A | 8/1985 | Rothfuss et al. |
| 4,545,377 A | 10/1985 | Cerwin et al. |
| 4,549,544 A | 10/1985 | Favaron |
| 4,556,058 A | 12/1985 | Green |
| 4,557,263 A | 12/1985 | Green |
| 4,562,839 A | 1/1986 | Blake, III et al. |
| 4,572,183 A | 2/1986 | Juska |
| 4,576,165 A | 3/1986 | Green et al. |
| 4,576,166 A | 3/1986 | Montgomery |
| 4,590,937 A | 5/1986 | Deniega |
| 4,598,711 A | 7/1986 | Deniega |
| 4,602,631 A | 7/1986 | Funatsu |
| 4,611,595 A | 9/1986 | Klieman et al. |
| 4,612,932 A | 9/1986 | Caspar et al. |
| 4,616,650 A | 10/1986 | Green et al. |
| 4,616,651 A | 10/1986 | Golden |
| 4,624,254 A | 11/1986 | McGarry et al. |
| 4,637,395 A | 1/1987 | Caspar et al. |
| 4,646,740 A | 3/1987 | Peters et al. |
| 4,647,504 A | 3/1987 | Kimimura et al. |
| 4,658,822 A | 4/1987 | Kees, Jr. |
| 4,660,558 A | 4/1987 | Kees, Jr. |
| 4,662,373 A | 5/1987 | Montgomery |
| 4,662,374 A | 5/1987 | Blake, III |
| 4,671,278 A | 6/1987 | Chin |
| 4,671,282 A | 6/1987 | Tretbar |
| 4,674,504 A | 6/1987 | Klieman et al. |
| 4,681,107 A | 7/1987 | Kees, Jr. |
| 4,696,396 A | 9/1987 | Samuels |
| 4,702,247 A | 10/1987 | Blake, III et al. |
| 4,706,668 A | 11/1987 | Backer |
| 4,712,549 A | 12/1987 | Peters |
| 4,733,664 A | 3/1988 | Kirsch et al. |
| 4,733,666 A | 3/1988 | Mercer, Jr. |
| 4,759,364 A | 7/1988 | Boebel |
| 4,765,335 A | 8/1988 | Schmidt et al. |
| 4,777,949 A | 10/1988 | Perlin |
| 4,777,950 A | 10/1988 | Kees, Jr. |
| 4,796,625 A | 1/1989 | Kees, Jr. |
| 4,799,481 A | 1/1989 | Transue et al. |
| 4,815,466 A | 3/1989 | Perlin |
| 4,817,604 A | 4/1989 | Smith, III |
| 4,821,721 A | 4/1989 | Chin et al. |
| 4,822,348 A | 4/1989 | Casey |
| 4,827,930 A | 5/1989 | Kees, Jr. |
| 4,834,096 A | 5/1989 | Oh et al. |
| 4,850,355 A | 7/1989 | Brooks et al. |
| 4,854,317 A | 8/1989 | Braun |
| 4,856,517 A | 8/1989 | Collins et al. |
| 4,929,239 A | 5/1990 | Braun |
| 4,929,240 A | 5/1990 | Kirsch et al. |
| 4,931,058 A | 6/1990 | Cooper |
| 4,932,955 A | 6/1990 | Merz et al. |
| 4,934,364 A | 6/1990 | Green |
| 4,943,298 A | 7/1990 | Fujita et al. |
| 4,957,500 A | 9/1990 | Liang et al. |
| 4,966,603 A | 10/1990 | Focelle et al. |
| 4,967,949 A | 11/1990 | Sandhaus |
| 4,983,176 A | 1/1991 | Cushman et al. |
| 4,988,355 A | 1/1991 | Leveen et al. |
| 5,002,552 A | 3/1991 | Casey |
| 5,026,379 A | 6/1991 | Yoon |
| 5,030,224 A | 7/1991 | Wright et al. |
| 5,030,226 A | 7/1991 | Green et al. |
| 5,032,127 A | 7/1991 | Frazee et al. |
| 5,035,692 A | 7/1991 | Lyon et al. |
| 5,047,038 A | 9/1991 | Peters et al. |
| 5,049,152 A | 9/1991 | Simon |
| 5,049,153 A | 9/1991 | Nakao et al. |
| 5,053,045 A | 10/1991 | Schmidt et al. |
| 5,059,202 A | 10/1991 | Liang et al. |
| 5,062,846 A | 11/1991 | Oh et al. |
| 5,078,731 A | 1/1992 | Hayhurst |
| 5,084,057 A | 1/1992 | Green et al. |
| 5,100,416 A | 3/1992 | Oh et al. |
| 5,100,420 A | 3/1992 | Green et al. |
| 5,104,394 A | 4/1992 | Knoepfler |
| 5,104,395 A | 4/1992 | Thornton et al. |
| 5,112,343 A | 5/1992 | Thornton |
| 5,122,150 A | 6/1992 | Puig |
| 5,127,915 A | 7/1992 | Mattson |
| 5,129,885 A | 7/1992 | Green et al. |
| 5,156,608 A | 10/1992 | Troidl et al. |
| 5,160,339 A | 11/1992 | Chen et al. |
| 5,163,945 A | 11/1992 | Ortiz et al. |
| 5,171,247 A | 12/1992 | Hughett et al. |
| 5,171,249 A | 12/1992 | Stefanchik |
| 5,171,250 A | 12/1992 | Yoon |
| 5,171,251 A | 12/1992 | Bregen et al. |
| 5,171,252 A | 12/1992 | Friedland |
| 5,171,253 A | 12/1992 | Klieman |
| 5,192,288 A | 3/1993 | Thompson et al. |
| 5,197,970 A | 3/1993 | Green et al. |
| 5,199,566 A | 4/1993 | Ortiz et al. |
| 5,201,746 A | 4/1993 | Shichman |
| 5,201,900 A | 4/1993 | Nardella |
| 5,207,691 A | 5/1993 | Nardella |
| 5,207,692 A | 5/1993 | Kraus et al. |
| 5,217,473 A | 6/1993 | Yoon |
| 5,219,353 A | 6/1993 | Garvey, III et al. |
| 5,246,450 A | 9/1993 | Thornton et al. |
| 5,269,792 A | 12/1993 | Kovac et al. |
| 5,281,228 A | 1/1994 | Wolfson |
| 5,282,807 A | 2/1994 | Knoepfler |
| 5,282,808 A | 2/1994 | Kovac et al. |
| 5,282,832 A | 2/1994 | Toso et al. |
| 5,289,963 A | 3/1994 | McGarry et al. |
| 5,290,299 A | 3/1994 | Fain et al. |
| 5,300,081 A | 4/1994 | Young et al. |
| 5,304,183 A | 4/1994 | Gourlay et al. |
| 5,306,280 A | 4/1994 | Bregen et al. |
| 5,306,283 A | 4/1994 | Conners |
| 5,312,426 A | 5/1994 | Segawa et al. |
| 5,330,442 A | 7/1994 | Green et al. |
| 5,330,487 A | 7/1994 | Thornton et al. |
| 5,340,360 A | 8/1994 | Stefanchik |
| 5,342,373 A | 8/1994 | Stefanchik et al. |
| 5,354,304 A | 10/1994 | Allen |
| 5,354,306 A | 10/1994 | Garvey, III et al. |
| 5,366,458 A | 11/1994 | Korthoff et al. |
| 5,366,459 A | 11/1994 | Yoon |
| 5,368,600 A | 11/1994 | Failla et al. |
| 5,381,943 A | 1/1995 | Allen et al. |
| 5,382,253 A | 1/1995 | Hogendijk |
| 5,382,254 A | 1/1995 | McGarry |
| 5,382,255 A | 1/1995 | Castro |
| 5,383,881 A | 1/1995 | Green |
| 5,395,375 A | 3/1995 | Turkel et al. |
| 5,395,381 A | 3/1995 | Green |
| 5,403,327 A | 4/1995 | Thornton et al. |
| 5,409,498 A | 4/1995 | Braddock et al. |
| 5,413,584 A | 5/1995 | Scjulze |
| 5,423,835 A | 6/1995 | Green |
| 5,425,740 A | 6/1995 | Hutchinson, Jr. |
| 5,431,667 A | 7/1995 | Thompson |
| 5,431,668 A | 7/1995 | Burbank, III et al. |
| 5,431,669 A | 7/1995 | Thompson |

(56) References Cited

U.S. PATENT DOCUMENTS

| | | |
|---|---|---|
| 5,439,468 A | 8/1995 | Schulze et al. |
| 5,441,509 A | 8/1995 | Vidal |
| 5,447,513 A | 9/1995 | Davison et al. |
| 5,449,365 A | 9/1995 | Green |
| 5,462,555 A | 10/1995 | Bolanos |
| 5,462,558 A | 10/1995 | Kolesa |
| 5,464,416 A | 11/1995 | Steckel |
| 5,474,566 A | 12/1995 | Alesi |
| 5,474,567 A | 12/1995 | Stefanchik et al. |
| 5,474,572 A | 12/1995 | Hayhurst |
| 5,487,746 A | 1/1996 | Yu et al. |
| 5,501,693 A | 3/1996 | Gravener |
| 5,509,920 A | 4/1996 | Phillips |
| 5,514,149 A | 5/1996 | Green |
| 5,520,701 A | 5/1996 | Lerch |
| 5,522,823 A | 6/1996 | Kuntz et al. |
| 5,527,318 A | 6/1996 | McGarry |
| 5,527,319 A | 6/1996 | Green |
| 5,527,320 A | 6/1996 | Carruthers et al. |
| 5,542,949 A | 8/1996 | Yoon |
| 5,547,474 A | 8/1996 | Kloeckl |
| 5,569,274 A | 10/1996 | Rapacki et al. |
| 5,571,121 A | 11/1996 | Heifetz |
| 5,575,802 A | 11/1996 | McQuilkin et al. |
| 5,582,615 A | 12/1996 | Foshee et al. |
| 5,584,840 A | 12/1996 | Ramsey et al. |
| 5,591,178 A | 1/1997 | Green et al. |
| 5,593,414 A | 1/1997 | Shipp et al. |
| 5,593,421 A | 1/1997 | Bauer |
| 5,601,573 A | 2/1997 | Fogelberg et al. |
| 5,601,574 A | 2/1997 | Stefanchik et al. |
| 5,607,436 A | 3/1997 | Pratt |
| 5,618,291 A | 4/1997 | Thompson |
| 5,618,306 A | 4/1997 | Roth et al. |
| 5,620,452 A | 4/1997 | Yoon |
| 5,626,585 A | 5/1997 | Mittelstadt |
| 5,626,586 A | 5/1997 | Pistl et al. |
| 5,626,587 A | 5/1997 | Bishop et al. |
| 5,626,592 A | 5/1997 | Phillips |
| RE35,525 E | 6/1997 | Stefanchik et al. |
| 5,634,930 A | 6/1997 | Thornton et al. |
| 5,643,291 A | 7/1997 | Pier |
| 5,645,551 A | 7/1997 | Green |
| 5,645,553 A | 7/1997 | Kolesa |
| 5,649,937 A | 7/1997 | Bito et al. |
| 5,653,720 A | 8/1997 | Johnson et al. |
| 5,662,676 A | 9/1997 | Koninckx |
| 5,662,679 A | 9/1997 | Voss et al. |
| 5,665,097 A | 9/1997 | Baker et al. |
| 5,676,676 A | 10/1997 | Porter |
| 5,681,330 A | 10/1997 | Hughett et al. |
| 5,683,405 A | 11/1997 | Yacoubian et al. |
| 5,695,502 A | 12/1997 | Pier |
| 5,695,505 A | 12/1997 | Yoon |
| 5,697,938 A | 12/1997 | Jensen et al. |
| 5,700,270 A | 12/1997 | Peyser |
| 5,700,271 A | 12/1997 | Whitfield |
| 5,702,048 A | 12/1997 | Eberlin |
| 5,709,706 A | 1/1998 | Kienzle et al. |
| 5,713,911 A | 2/1998 | Racenet |
| 5,713,912 A | 2/1998 | Porter |
| 5,720,756 A | 2/1998 | Green |
| 5,722,982 A | 3/1998 | Ferreira et al. |
| 5,725,537 A | 3/1998 | Green |
| 5,725,538 A | 3/1998 | Green |
| 5,725,542 A | 3/1998 | Yoon |
| 5,733,295 A | 3/1998 | Back et al. |
| 5,755,726 A | 5/1998 | Pratt |
| 5,766,189 A | 6/1998 | Matsuno |
| 5,769,857 A | 6/1998 | Reztzov et al. |
| 5,772,673 A | 6/1998 | Cuny |
| 5,776,146 A | 7/1998 | Sackier et al. |
| 5,776,147 A | 7/1998 | Dolendo |
| 5,779,718 A | 7/1998 | Green |
| 5,779,720 A | 7/1998 | Walder-Utz et al. |
| 5,782,844 A | 7/1998 | Yoon et al. |
| 5,788,698 A | 8/1998 | Savornin |
| 5,792,149 A | 8/1998 | Sherts |
| 5,792,150 A | 8/1998 | Pratt |
| 5,797,922 A | 8/1998 | Hessel et al. |
| 5,810,853 A | 9/1998 | Yoon |
| 5,817,116 A | 10/1998 | Takahashi et al. |
| 5,827,306 A | 10/1998 | Yoon |
| 5,833,695 A | 11/1998 | Yoon |
| 5,833,696 A | 11/1998 | Whitfield |
| 5,833,700 A | 11/1998 | Fogelberg et al. |
| 5,835,199 A | 11/1998 | Phillips |
| 5,843,097 A | 12/1998 | Mayenberger et al. |
| 5,843,101 A | 12/1998 | Fry |
| 5,846,255 A | 12/1998 | Casey |
| 5,849,019 A | 12/1998 | Yoon |
| 5,858,018 A | 1/1999 | Shipp et al. |
| 5,861,005 A | 1/1999 | Kontos |
| 5,868,759 A | 2/1999 | Peyser |
| 5,868,761 A | 2/1999 | Nicholas |
| 5,876,410 A | 3/1999 | Petillo |
| 5,895,394 A | 4/1999 | Kienzle et al. |
| 5,897,565 A | 4/1999 | Foster |
| 5,904,693 A | 5/1999 | Dicesare |
| 5,913,862 A | 6/1999 | Ramsey et al. |
| 5,918,791 A | 7/1999 | Sorrentino et al. |
| 5,921,996 A | 7/1999 | Sherman |
| 5,921,997 A | 7/1999 | Fogelberg et al. |
| 5,928,251 A | 7/1999 | Aranyi |
| 5,938,667 A | 8/1999 | Peyser |
| 5,951,574 A | 9/1999 | Stefanchik et al. |
| 5,972,003 A | 10/1999 | Rousseau |
| 5,976,159 A | 11/1999 | Bolduc et al. |
| 5,993,465 A | 11/1999 | Shipp et al. |
| 6,004,335 A | 12/1999 | Vaitekunas et al. |
| 6,017,358 A | 1/2000 | Yoon et al. |
| 6,045,560 A | 4/2000 | McKean et al. |
| RE36,720 E | 5/2000 | Green |
| 6,059,799 A | 5/2000 | Aranyi |
| 6,099,536 A | 8/2000 | Petillo |
| 6,099,537 A | 8/2000 | Sugai et al. |
| 6,139,555 A | 10/2000 | Hart et al. |
| 6,210,418 B1 | 4/2001 | Storz et al. |
| 6,217,590 B1 | 4/2001 | Levinson |
| 6,228,097 B1 | 5/2001 | Levinson et al. |
| 6,241,740 B1 | 6/2001 | Davis |
| 6,258,105 B1 | 7/2001 | Hart et al. |
| 6,261,302 B1 | 7/2001 | Voegele et al. |
| 6,273,898 B1 | 8/2001 | Kienzle et al. |
| 6,277,131 B1 | 8/2001 | Kalikow |
| 6,306,149 B1 | 10/2001 | Meade |
| 6,318,619 B1 | 11/2001 | Lee |
| 6,322,571 B1 | 11/2001 | Adams |
| 6,350,269 B1 | 2/2002 | Shipp et al. |
| 6,352,541 B1 | 3/2002 | Kienzle et al. |
| 6,391,035 B1 | 5/2002 | Appleby et al. |
| 6,423,079 B1 | 7/2002 | Blake, III |
| 6,428,548 B1 | 8/2002 | Durgin et al. |
| 6,440,144 B1 | 8/2002 | Bacher |
| 6,461,363 B1 | 10/2002 | Gadberry et al. |
| 6,464,710 B1 | 10/2002 | Foster |
| 6,494,886 B1 | 12/2002 | Wilk et al. |
| 6,517,536 B2 | 2/2003 | Hooven et al. |
| 6,520,972 B2 | 2/2003 | Peters |
| 6,527,786 B1 | 3/2003 | Davis |
| 6,537,289 B1 | 3/2003 | Kayan |
| 6,546,935 B2 | 4/2003 | Hooven |
| 6,551,333 B2 | 4/2003 | Kuhns et al. |
| 6,569,171 B2 | 5/2003 | DeGuillebon et al. |
| 6,579,304 B1 | 6/2003 | Hart et al. |
| 6,599,298 B1 | 7/2003 | Forster et al. |
| 6,602,252 B2 | 8/2003 | Mollenauer |
| 6,607,540 B1 | 8/2003 | Shipp |
| 6,613,060 B2 | 9/2003 | Adams et al. |
| 6,626,916 B1 | 9/2003 | Yeung et al. |
| 6,626,922 B1 | 9/2003 | Hart et al. |
| 6,648,898 B1 | 11/2003 | Baxter |
| 6,652,538 B2 | 11/2003 | Kayan et al. |
| 6,652,539 B2 | 11/2003 | Shipp et al. |

(56) References Cited

U.S. PATENT DOCUMENTS

| | | |
|---|---|---|
| 6,656,193 B2 | 12/2003 | Grant et al. |
| 6,673,083 B1 | 1/2004 | Kayan |
| 6,676,659 B2 | 1/2004 | Hutchins et al. |
| 6,679,894 B2 | 1/2004 | Damarati |
| RE38,445 E | 2/2004 | Pistl |
| 6,695,854 B1 | 2/2004 | Kayan |
| 6,706,057 B1 | 3/2004 | Bidoia et al. |
| 6,716,226 B2 | 4/2004 | Sixto, Jr. et al. |
| 6,723,109 B2 | 4/2004 | Solingen |
| 6,743,240 B2 | 6/2004 | Smith et al. |
| 6,773,438 B1 | 8/2004 | Knodel et al. |
| 6,773,440 B2 | 8/2004 | Gannoe et al. |
| 6,776,783 B1 | 8/2004 | Frantzen et al. |
| 6,776,784 B2 | 8/2004 | Ginn |
| 6,780,195 B2 | 8/2004 | Porat |
| 6,793,663 B2 | 9/2004 | Kneifel et al. |
| 6,793,664 B2 | 9/2004 | Mazzocchi et al. |
| 6,802,848 B2 | 10/2004 | Anderson et al. |
| 6,814,742 B2 | 11/2004 | Kimura et al. |
| 6,818,009 B2 | 11/2004 | Hart et al. |
| 6,821,273 B2 | 11/2004 | Mollenauer |
| 6,821,284 B2 | 11/2004 | Sturtz et al. |
| 6,824,547 B2 | 11/2004 | Wilson, Jr. et al. |
| 6,824,548 B2 | 11/2004 | Smith et al. |
| 6,835,199 B2 | 12/2004 | McGuckin, Jr. et al. |
| 6,835,200 B2 | 12/2004 | Laufer et al. |
| 6,837,893 B2 | 1/2005 | Miller |
| 6,837,894 B2 | 1/2005 | Pugsley, Jr. et al. |
| 6,837,895 B2 | 1/2005 | Mayenberger |
| 6,840,945 B2 | 1/2005 | Manetakis et al. |
| 6,843,794 B2 | 1/2005 | Sixto, Jr. et al. |
| 6,849,078 B2 | 2/2005 | Durgin et al. |
| 6,849,079 B1 | 2/2005 | Blake, III et al. |
| 6,853,879 B2 | 2/2005 | Sunaoshi |
| 6,869,435 B2 | 3/2005 | Blake, III |
| 6,869,436 B2 | 3/2005 | Wendlandt |
| 6,889,116 B2 | 5/2005 | Jinno |
| 6,896,682 B1 | 5/2005 | McClellan et al. |
| 6,905,503 B2 | 6/2005 | Gifford, III et al. |
| 6,911,032 B2 | 6/2005 | Jugenheimer et al. |
| 6,911,033 B2 | 6/2005 | de Guillebon et al. |
| 6,913,607 B2 | 7/2005 | Ainsworth et al. |
| 6,916,327 B2 | 7/2005 | Northrup, III et al. |
| 6,923,818 B2 | 8/2005 | Muramatsu et al. |
| 6,939,356 B2 | 9/2005 | Debbas |
| 6,942,674 B2 | 9/2005 | Belef et al. |
| 6,942,676 B2 | 9/2005 | Buelna |
| 6,945,978 B1 | 9/2005 | Hyde |
| 6,945,979 B2 | 9/2005 | Kortenbach et al. |
| 6,949,107 B2 | 9/2005 | McGuckin, Jr. et al. |
| 6,953,465 B2 | 10/2005 | Dieck et al. |
| 6,955,643 B2 | 10/2005 | Gellman et al. |
| 6,959,852 B2 | 11/2005 | Shelton, IV et al. |
| 6,960,218 B2 | 11/2005 | Rennich |
| 6,960,221 B2 | 11/2005 | Ho et al. |
| 6,962,594 B1 | 11/2005 | Thevenet |
| 6,963,792 B1 | 11/2005 | Green |
| 6,964,363 B2 | 11/2005 | Wales et al. |
| 6,964,668 B2 | 11/2005 | Modesitt et al. |
| 6,966,875 B1 | 11/2005 | Longobardi |
| 6,966,917 B1 | 11/2005 | Suyker et al. |
| 6,966,919 B2 | 11/2005 | Sixto, Jr. et al. |
| 6,969,391 B1 | 11/2005 | Gazzani |
| 6,972,023 B2 | 12/2005 | Whayne et al. |
| 6,972,027 B2 | 12/2005 | Fallin et al. |
| 6,973,770 B2 | 12/2005 | Schnipke et al. |
| 6,974,462 B2 | 12/2005 | Sater |
| 6,974,466 B2 | 12/2005 | Ahmed et al. |
| 6,974,475 B1 | 12/2005 | Wall |
| 6,981,505 B2 | 1/2006 | Krause et al. |
| 6,981,628 B2 | 1/2006 | Wales |
| 6,991,635 B2 | 1/2006 | Takamoto et al. |
| 7,052,504 B2 | 5/2006 | Hughett |
| 7,056,330 B2 | 6/2006 | Gayton |
| 7,108,703 B2 | 9/2006 | Danitz et al. |
| 7,144,402 B2 | 12/2006 | Kuester, III |
| 7,175,648 B2 | 2/2007 | Nakao |
| 7,179,265 B2 | 2/2007 | Manetakis et al. |
| 7,207,997 B2 | 4/2007 | Shipp et al. |
| 7,211,091 B2 | 5/2007 | Fowler et |
| 7,211,092 B2 | 5/2007 | Hughett |
| 7,214,230 B2 | 5/2007 | Brock et al. |
| 7,214,232 B2 | 5/2007 | Bowman et al. |
| 7,223,271 B2 | 5/2007 | Muramatsu et al. |
| 7,223,272 B2 | 5/2007 | Francese et al. |
| 7,232,445 B2 | 6/2007 | Kortenbach et al. |
| 7,261,724 B2 | 8/2007 | Molitor et al. |
| 7,261,725 B2 | 8/2007 | Binmoeller |
| 7,264,625 B1 | 9/2007 | Buncke |
| 7,288,098 B2 | 10/2007 | Huitema et al. |
| 7,297,149 B2 | 11/2007 | Vitali et al. |
| 7,316,693 B2 | 1/2008 | Viola |
| 7,316,696 B2 | 1/2008 | Wilson, Jr. et al. |
| 7,326,223 B2 | 2/2008 | Wilson, Jr. |
| 7,329,266 B2 | 2/2008 | Royse et al. |
| 7,331,968 B2 | 2/2008 | Arp et al. |
| 7,338,503 B2 | 3/2008 | Rosenberg et al. |
| 7,357,805 B2 | 4/2008 | Masuda et al. |
| 7,510,562 B2 | 3/2009 | Lindsay |
| 7,552,853 B2 | 6/2009 | Mas et al. |
| 7,637,917 B2 | 12/2009 | Whitfield |
| 7,686,820 B2 | 3/2010 | Huitema et al. |
| 7,695,482 B2 | 4/2010 | Viola |
| 7,717,926 B2 | 5/2010 | Whitfield |
| 7,727,248 B2 | 6/2010 | Smith et al. |
| 7,731,724 B2 | 6/2010 | Huitema et al. |
| 7,740,641 B2 | 6/2010 | Huitema |
| 7,752,853 B2 | 7/2010 | Singh et al. |
| 7,753,250 B2 | 7/2010 | Clauson et al. |
| 7,819,886 B2 | 10/2010 | Whitfield |
| 7,887,553 B2 | 2/2011 | Lehman et al. |
| 7,905,890 B2 | 3/2011 | Whitfield |
| 7,942,885 B2 | 5/2011 | Sixto, Jr. et al. |
| 7,963,433 B2 | 6/2011 | Whitman et al. |
| 7,988,027 B2 | 8/2011 | Olson |
| 8,011,550 B2 | 9/2011 | Aranyi |
| 8,011,555 B2 | 9/2011 | Tarinelli |
| 8,016,178 B2 | 9/2011 | Olson |
| 8,021,375 B2 | 9/2011 | Aldrich |
| 8,021,378 B2 | 9/2011 | Sixto, Jr. |
| 8,038,686 B2 | 10/2011 | Huitema et al. |
| 8,056,565 B2 | 11/2011 | Zergiebel |
| 8,062,310 B2 | 11/2011 | Shibata et al. |
| 8,066,720 B2 | 11/2011 | Knodel et al. |
| 8,066,721 B2 | 11/2011 | Kortenbach et al. |
| 8,066,722 B2 | 11/2011 | Miyagi et al. |
| 8,070,760 B2 | 12/2011 | Fujita |
| 8,075,571 B2 | 12/2011 | Vitali et al. |
| 8,080,021 B2 | 12/2011 | Griego |
| 8,083,668 B2 | 12/2011 | Durgin |
| 8,088,061 B2 | 1/2012 | Wells |
| 8,091,755 B2 | 1/2012 | Kayan |
| 8,100,926 B1 | 1/2012 | Filshie et al. |
| 8,128,643 B2 | 3/2012 | Aranyi |
| 8,133,240 B2 | 3/2012 | Damarati |
| 8,142,451 B2 | 3/2012 | Boulnois |
| 8,157,149 B2 | 4/2012 | Olson |
| 8,157,151 B2 | 4/2012 | Ingmanson |
| 8,172,859 B2 | 5/2012 | Matsuno et al. |
| 8,172,870 B2 | 5/2012 | Shipp |
| 8,187,290 B2 | 5/2012 | Buckman et al. |
| 8,211,120 B2 | 7/2012 | Itoh |
| 8,211,124 B2 | 7/2012 | Ainsworth et al. |
| 8,216,255 B2 | 7/2012 | Smith et al. |
| 8,216,257 B2 | 7/2012 | Huitema |
| 8,236,012 B2 | 8/2012 | Molitor |
| 8,246,634 B2 | 8/2012 | Huitema |
| 8,246,635 B2 | 8/2012 | Huitema |
| 8,262,678 B2 | 9/2012 | Matsuoka et al. |
| 8,262,679 B2 | 9/2012 | Nguyen |
| 8,267,944 B2 | 9/2012 | Sorrentino |
| 8,267,945 B2 | 9/2012 | Nguyen |
| 8,267,946 B2 | 9/2012 | Whitfield |
| 8,282,655 B2 | 10/2012 | Whitfield |

(56) References Cited

U.S. PATENT DOCUMENTS

| | | |
|---|---|---|
| 8,308,743 B2 | 11/2012 | Matsuno et al. |
| 8,328,822 B2 | 12/2012 | Huitema |
| 8,336,556 B2 | 12/2012 | Zergiebel |
| 8,348,130 B2 | 1/2013 | Shah |
| 8,357,171 B2 | 1/2013 | Whitfield |
| 8,366,726 B2 | 2/2013 | Dennis |
| 8,371,491 B2 | 2/2013 | Huitema |
| 8,372,095 B2 | 2/2013 | Viola |
| 8,382,773 B2 | 2/2013 | Whitfield |
| 8,398,655 B2 | 3/2013 | Cheng et al. |
| 8,403,945 B2 | 3/2013 | Whitfield |
| 8,403,946 B2 | 3/2013 | Whitfield |
| 8,409,222 B2 | 4/2013 | Whitfield |
| 8,409,223 B2 | 4/2013 | Sorrentino |
| 8,419,752 B2 | 4/2013 | Sorrentino |
| 8,430,892 B2 | 4/2013 | Bindra |
| 8,444,660 B2 | 5/2013 | Adams |
| 8,465,502 B2 | 6/2013 | Zergiebel |
| 8,475,473 B2 | 7/2013 | Vandenbroek |
| 8,480,688 B2 | 7/2013 | Boulnois |
| 8,486,091 B2 | 7/2013 | Sorrentino |
| 8,491,608 B2 | 7/2013 | Sorrentino |
| 8,496,673 B2 | 7/2013 | Nguyen |
| 8,506,580 B2 | 8/2013 | Zergiebel |
| 8,512,357 B2 | 8/2013 | Viola |
| 8,523,882 B2 | 9/2013 | Huitema |
| 8,529,585 B2 | 9/2013 | Jacobs |
| 8,529,586 B2 | 9/2013 | Rosenberg |
| 8,529,588 B2 | 9/2013 | Ahlberg |
| 8,545,486 B2 | 10/2013 | Malkowski |
| 8,556,920 B2 | 10/2013 | Huitema et al. |
| 8,568,430 B2 | 10/2013 | Shipp |
| 8,579,918 B2 | 11/2013 | Whitfield |
| 8,585,717 B2 | 11/2013 | Sorrentino |
| 8,603,109 B2 | 12/2013 | Aranyi |
| 8,623,044 B2 | 1/2014 | Timm et al. |
| 8,652,151 B2 | 2/2014 | Lehman et al. |
| 8,652,152 B2 | 2/2014 | Aranyi et al. |
| 8,663,247 B2 | 3/2014 | Menn et al. |
| 8,685,048 B2 | 4/2014 | Adams et al. |
| 8,690,899 B2 | 4/2014 | Kogiso et al. |
| 8,709,027 B2 | 4/2014 | Adams et al. |
| 8,720,766 B2 | 5/2014 | Hess et al. |
| 8,734,469 B2 | 5/2014 | Pribanic et al. |
| 8,747,423 B2 | 6/2014 | Whitfield et al. |
| 8,753,356 B2 | 6/2014 | Vitali et al. |
| 8,814,884 B2 | 8/2014 | Whitfield et al. |
| 8,821,516 B2 | 9/2014 | Huitema |
| 8,839,954 B2 | 9/2014 | Disch |
| 8,845,659 B2 | 9/2014 | Whitfield et al. |
| 8,894,665 B2 | 11/2014 | Sorrentino et al. |
| 8,894,666 B2 | 11/2014 | Schulz et al. |
| 8,920,438 B2 | 12/2014 | Aranyi et al. |
| 8,961,542 B2 | 2/2015 | Whitfield et al. |
| 8,968,337 B2 | 3/2015 | Whitfield et al. |
| 8,973,804 B2 | 3/2015 | Hess et al. |
| 9,011,464 B2 | 4/2015 | Zammataro |
| 9,011,465 B2 | 4/2015 | Whitfield et al. |
| 2001/0047178 A1 | 11/2001 | Peters |
| 2002/0040226 A1 | 4/2002 | Laufer et al. |
| 2002/0068947 A1 | 6/2002 | Kuhns et al. |
| 2002/0082618 A1 | 6/2002 | Shipp et al. |
| 2002/0087169 A1 | 7/2002 | Brock et al. |
| 2002/0087170 A1 | 7/2002 | Kuhns et al. |
| 2002/0099388 A1 | 7/2002 | Mayenberger |
| 2002/0120279 A1 | 8/2002 | Deguillebon et al. |
| 2002/0128668 A1 | 9/2002 | Manetakis et al. |
| 2002/0177859 A1 | 11/2002 | Monassevitch et al. |
| 2002/0198537 A1 | 12/2002 | Smith et al. |
| 2002/0198538 A1 | 12/2002 | Kortenbach et al. |
| 2002/0198539 A1 | 12/2002 | Sixto, Jr. et al. |
| 2002/0198540 A1 | 12/2002 | Smith et al. |
| 2002/0198541 A1 | 12/2002 | Smith et al. |
| 2003/0014060 A1 | 1/2003 | Wilson, Jr. et al. |
| 2003/0018345 A1 | 1/2003 | Green |
| 2003/0023249 A1 | 1/2003 | Manetakis |
| 2003/0040759 A1 | 2/2003 | de Guillebon et al. |
| 2003/0105476 A1 | 6/2003 | Sancoff et al. |
| 2003/0114867 A1 | 6/2003 | Bolduc et al. |
| 2003/0135224 A1 | 7/2003 | Blake, III |
| 2003/0167063 A1 | 9/2003 | Kerr |
| 2003/0208231 A1 | 11/2003 | Williamson, IV et al. |
| 2003/0220657 A1 | 11/2003 | Adams |
| 2003/0225423 A1 | 12/2003 | Huitema |
| 2003/0229360 A1 | 12/2003 | Gayton |
| 2003/0233105 A1 | 12/2003 | Gayton |
| 2004/0010272 A1 | 1/2004 | Manetakis et al. |
| 2004/0044352 A1 | 3/2004 | Fowler et al. |
| 2004/0097970 A1 | 5/2004 | Hughett |
| 2004/0097971 A1 | 5/2004 | Hughett |
| 2004/0097972 A1 | 5/2004 | Shipp et al. |
| 2004/0106936 A1 | 6/2004 | Shipp et al. |
| 2004/0133215 A1 | 7/2004 | Baxter |
| 2004/0138681 A1 | 7/2004 | Pier |
| 2004/0153100 A1 | 8/2004 | Ahlberg et al. |
| 2004/0158266 A1 | 8/2004 | Damarati |
| 2004/0162567 A9 | 8/2004 | Adams |
| 2004/0167545 A1 | 8/2004 | Sadler et al. |
| 2004/0176776 A1 | 9/2004 | Zubok et al. |
| 2004/0176783 A1 | 9/2004 | Edoga et al. |
| 2004/0176784 A1 | 9/2004 | Okada |
| 2004/0193213 A1 | 9/2004 | Aranyi |
| 2005/0080440 A1 | 4/2005 | Durgin et al. |
| 2005/0085830 A1 | 4/2005 | Lehman et al. |
| 2005/0090837 A1 | 4/2005 | Sixto, Jr. et al. |
| 2005/0090838 A1 | 4/2005 | Sixto, Jr. et al. |
| 2005/0096670 A1 | 5/2005 | Wellman et al. |
| 2005/0096671 A1 | 5/2005 | Wellman et al. |
| 2005/0096672 A1 | 5/2005 | Manetakis et al. |
| 2005/0101975 A1 | 5/2005 | Nguyen et al. |
| 2005/0107807 A1 | 5/2005 | Nakao |
| 2005/0107809 A1 | 5/2005 | Litscher et al. |
| 2005/0107810 A1 | 5/2005 | Morales et al. |
| 2005/0107811 A1 | 5/2005 | Starksen et al. |
| 2005/0107812 A1 | 5/2005 | Starksen et al. |
| 2005/0107871 A1 | 5/2005 | Realyvasquez et al. |
| 2005/0113847 A1 | 5/2005 | Gadberry et al. |
| 2005/0119671 A1 | 6/2005 | Reydel et al. |
| 2005/0119673 A1 | 6/2005 | Gordon et al. |
| 2005/0119677 A1 | 6/2005 | Shipp |
| 2005/0125010 A1 | 6/2005 | Smith et al. |
| 2005/0143767 A1 | 6/2005 | Kimura et al. |
| 2005/0149063 A1 | 7/2005 | Young et al. |
| 2005/0149064 A1 | 7/2005 | Peterson et al. |
| 2005/0149068 A1 | 7/2005 | Williams et al. |
| 2005/0149069 A1 | 7/2005 | Bertolero et al. |
| 2005/0165415 A1 | 7/2005 | Wales |
| 2005/0165418 A1 | 7/2005 | Chan |
| 2005/0171560 A1 | 8/2005 | Hughett |
| 2005/0175703 A1 | 8/2005 | Hunter |
| 2005/0177176 A1 | 8/2005 | Gerbi et al. |
| 2005/0177177 A1 | 8/2005 | Viola |
| 2005/0203547 A1 | 9/2005 | Weller et al. |
| 2005/0203548 A1 | 9/2005 | Weller et al. |
| 2005/0216036 A1 | 9/2005 | Nakao |
| 2005/0216056 A1 | 9/2005 | Valdevit et al. |
| 2005/0222588 A1 | 10/2005 | Vandenbroek et al. |
| 2005/0222590 A1 | 10/2005 | Gadberry et al. |
| 2005/0222665 A1 | 10/2005 | Aranyi |
| 2005/0228411 A1 | 10/2005 | Manzo |
| 2005/0228416 A1 | 10/2005 | Burbank et al. |
| 2005/0234478 A1 | 10/2005 | Wixey et al. |
| 2005/0251183 A1 | 11/2005 | Buckman et al. |
| 2005/0251184 A1 | 11/2005 | Anderson |
| 2005/0256529 A1 | 11/2005 | Yawata et al. |
| 2005/0267495 A1 | 12/2005 | Ginn et al. |
| 2005/0273122 A1 | 12/2005 | Theroux et al. |
| 2005/0277951 A1 | 12/2005 | Smith et al. |
| 2005/0277952 A1 | 12/2005 | Arp et al. |
| 2005/0277953 A1 | 12/2005 | Francese et al. |
| 2005/0277954 A1 | 12/2005 | Smith et al. |
| 2005/0277955 A1 | 12/2005 | Palmer et al. |
| 2005/0277956 A1 | 12/2005 | Francese et al. |
| 2005/0277958 A1 | 12/2005 | Levinson |

(56) References Cited

U.S. PATENT DOCUMENTS

| | | |
|---|---|---|
| 2005/0288689 A1 | 12/2005 | Kammerer et al. |
| 2005/0288690 A1 | 12/2005 | Bourque et al. |
| 2006/0004388 A1 | 1/2006 | Whayne et al. |
| 2006/0004390 A1 | 1/2006 | Rosenberg et al. |
| 2006/0009789 A1 | 1/2006 | Gambale et al. |
| 2006/0009790 A1 | 1/2006 | Blake, III et al. |
| 2006/0009792 A1 | 1/2006 | Baker et al. |
| 2006/0020270 A1 | 1/2006 | Jabba et al. |
| 2006/0020271 A1 | 1/2006 | Stewart et al. |
| 2006/0047305 A1 | 3/2006 | Ortiz et al. |
| 2006/0047306 A1 | 3/2006 | Ortiz et al. |
| 2006/0064117 A1 | 3/2006 | Aranyi et al. |
| 2006/0079115 A1 | 4/2006 | Aranyi |
| 2006/0079912 A1 | 4/2006 | Whitfield et al. |
| 2006/0079913 A1 | 4/2006 | Whitfield et al. |
| 2006/0085015 A1 | 4/2006 | Whitfield et al. |
| 2006/0100649 A1 | 5/2006 | Hart |
| 2006/0111731 A1 | 5/2006 | Manzo |
| 2006/0129170 A1 | 6/2006 | Royce et al. |
| 2006/0135992 A1 | 6/2006 | Bettuchi et al. |
| 2006/0163312 A1 | 7/2006 | Viola et al. |
| 2006/0173470 A1 | 8/2006 | Oray et al. |
| 2006/0178683 A1 | 8/2006 | Shimoji et al. |
| 2006/0184182 A1 | 8/2006 | Aranyi et al. |
| 2006/0190013 A1 | 8/2006 | Menn |
| 2006/0195125 A1 | 8/2006 | Sakakine et al. |
| 2006/0200179 A1 | 9/2006 | Barker et al. |
| 2006/0212050 A1 | 9/2006 | D'Agostino et al. |
| 2006/0217749 A1 | 9/2006 | Wilson, Jr. et al. |
| 2006/0224165 A1 | 10/2006 | Surti |
| 2006/0224170 A1 | 10/2006 | Duff |
| 2006/0235437 A1 | 10/2006 | Vitali et al. |
| 2006/0235438 A1 | 10/2006 | Huitema et al. |
| 2006/0235439 A1 | 10/2006 | Molitor et al. |
| 2006/0235440 A1 | 10/2006 | Huitema et al. |
| 2006/0235441 A1 | 10/2006 | Huitema et al. |
| 2006/0235442 A1 | 10/2006 | Huitema |
| 2006/0235443 A1 | 10/2006 | Huitema et al. |
| 2006/0235444 A1 | 10/2006 | Huitema et al. |
| 2006/0259045 A1 | 11/2006 | Damarati |
| 2006/0259049 A1 | 11/2006 | Harada et al. |
| 2006/0264987 A1 | 11/2006 | Sgro |
| 2006/0271072 A1 | 11/2006 | Hummel et al. |
| 2007/0016228 A1 | 1/2007 | Salas |
| 2007/0021761 A1 | 1/2007 | Phillips |
| 2007/0023476 A1 | 2/2007 | Whitman et al. |
| 2007/0023477 A1 | 2/2007 | Whitman et al. |
| 2007/0027458 A1 | 2/2007 | Sixto, Jr. et al. |
| 2007/0034669 A1 | 2/2007 | De La Torre et al. |
| 2007/0038233 A1 | 2/2007 | Martinez et al. |
| 2007/0049947 A1 | 3/2007 | Menn et al. |
| 2007/0049948 A1 | 3/2007 | Menn et al. |
| 2007/0049949 A1 | 3/2007 | Manetakis |
| 2007/0049950 A1 | 3/2007 | Theroux et al. |
| 2007/0049951 A1 | 3/2007 | Menn |
| 2007/0049953 A2 | 3/2007 | Shimoji et al. |
| 2007/0066981 A1 | 3/2007 | Meagher |
| 2007/0073314 A1 | 3/2007 | Gadberry et al. |
| 2007/0083218 A1 | 4/2007 | Morris |
| 2007/0093856 A1 | 4/2007 | Whitfield |
| 2007/0106314 A1 | 5/2007 | Dunn |
| 2007/0112365 A1 | 5/2007 | Hilal et al. |
| 2007/0118155 A1 | 5/2007 | Goldfarb et al. |
| 2007/0118161 A1 | 5/2007 | Kennedy et al. |
| 2007/0118163 A1 | 5/2007 | Boudreaux et al. |
| 2007/0118174 A1 | 5/2007 | Chu |
| 2007/0123916 A1 | 5/2007 | Maier et al. |
| 2007/0142848 A1 | 6/2007 | Ainsworth et al. |
| 2007/0142851 A1 | 6/2007 | Sixto, Jr. et al. |
| 2007/0149988 A1 | 6/2007 | Michler et al. |
| 2007/0149989 A1 | 6/2007 | Santili et al. |
| 2007/0162060 A1 | 7/2007 | Wild |
| 2007/0173866 A1 | 7/2007 | Sorrentino et al. |
| 2007/0185504 A1 | 8/2007 | Manetakis et al. |
| 2007/0191868 A1 | 8/2007 | Theroux et al. |
| 2007/0203509 A1 | 8/2007 | Bettuchi |
| 2007/0203510 A1 | 8/2007 | Bettuchi |
| 2007/0213747 A1 | 9/2007 | Monassevitch et al. |
| 2007/0250080 A1 | 10/2007 | Jones et al. |
| 2007/0265640 A1 | 11/2007 | Kortenbach et al. |
| 2007/0276417 A1 | 11/2007 | Mendes, Jr. et al. |
| 2007/0282355 A1 | 12/2007 | Brown et al. |
| 2007/0288039 A1 | 12/2007 | Aranyi |
| 2007/0293875 A1 | 12/2007 | Soetikno et al. |
| 2008/0004636 A1 | 1/2008 | Walberg et al. |
| 2008/0004637 A1 | 1/2008 | Klassen et al. |
| 2008/0004639 A1 | 1/2008 | Huitema et al. |
| 2008/0015615 A1 | 1/2008 | Molitor et al. |
| 2008/0027465 A1 | 1/2008 | Vitali et al. |
| 2008/0027466 A1 | 1/2008 | Vitali et al. |
| 2008/0045981 A1 | 2/2008 | Margolin et al. |
| 2008/0051808 A1 | 2/2008 | Rivera et al. |
| 2008/0065118 A1 | 3/2008 | Damarati |
| 2008/0065119 A1 | 3/2008 | Viola |
| 2008/0140090 A1 | 6/2008 | Aranyi et al. |
| 2008/0147092 A1 | 6/2008 | Rogge et al. |
| 2008/0147093 A1 | 6/2008 | Roskopf et al. |
| 2008/0154287 A1 | 6/2008 | Rosenberg et al. |
| 2008/0167665 A1 | 7/2008 | Arp et al. |
| 2008/0228199 A1 | 9/2008 | Cropper et al. |
| 2008/0243145 A1 | 10/2008 | Whitfield et al. |
| 2008/0306492 A1 | 12/2008 | Shibata et al. |
| 2008/0306493 A1 | 12/2008 | Shibata et al. |
| 2008/0312665 A1 | 12/2008 | Shibata et al. |
| 2008/0319456 A1 | 12/2008 | Hart |
| 2009/0076533 A1 | 3/2009 | Kayan et al. |
| 2009/0088777 A1 | 4/2009 | Miyagi et al. |
| 2009/0088783 A1 | 4/2009 | Kennedy et al. |
| 2009/0171380 A1 | 7/2009 | Whiting |
| 2009/0222003 A1 | 9/2009 | Otley et al. |
| 2009/0228023 A1 | 9/2009 | Cui et al. |
| 2009/0228024 A1 | 9/2009 | Whitfield et al. |
| 2009/0264904 A1 | 10/2009 | Aldrich et al. |
| 2009/0299382 A1 | 12/2009 | Zergiebel |
| 2009/0326558 A1 | 12/2009 | Cui et al. |
| 2010/0049216 A1 | 2/2010 | Zergiebel |
| 2010/0057102 A1 | 3/2010 | Sorrentino et al. |
| 2010/0057103 A1 | 3/2010 | Sorrentino et al. |
| 2010/0057104 A1 | 3/2010 | Sorrentino et al. |
| 2010/0057105 A1 | 3/2010 | Sorrentino |
| 2010/0057106 A1 | 3/2010 | Sorrentino et al. |
| 2010/0057107 A1 | 3/2010 | Sorrentino et al. |
| 2010/0069935 A1* | 3/2010 | Crainich ............... 606/157 |
| 2010/0121351 A1 | 5/2010 | Whitfield |
| 2010/0137886 A1 | 6/2010 | Zergiebel |
| 2010/0204715 A1 | 8/2010 | Whitfield et al. |
| 2010/0222790 A1 | 9/2010 | Whitfield et al. |
| 2010/0274262 A1 | 10/2010 | Schulz et al. |
| 2010/0274264 A1 | 10/2010 | Schulz et al. |
| 2011/0028994 A1 | 2/2011 | Whitfield et al. |
| 2011/0054498 A1 | 3/2011 | Monassevitch et al. |
| 2011/0082474 A1 | 4/2011 | Bindra et al. |
| 2011/0087241 A1 | 4/2011 | Nguyen |
| 2011/0087242 A1 | 4/2011 | Pribanic |
| 2011/0087243 A1 | 4/2011 | Nguyen et al. |
| 2011/0112552 A1 | 5/2011 | Lehman et al. |
| 2011/0137323 A1 | 6/2011 | Malkowski |
| 2011/0137324 A1 | 6/2011 | Boudreaux et al. |
| 2011/0144662 A1 | 6/2011 | McLawhorn et al. |
| 2011/0144665 A1 | 6/2011 | Malkowski |
| 2011/0190791 A1 | 8/2011 | Jacobs et al. |
| 2011/0208211 A1 | 8/2011 | Whitfield et al. |
| 2011/0208212 A1 | 8/2011 | Zergiebel |
| 2011/0218553 A1 | 9/2011 | Huitema et al. |
| 2011/0218554 A1 | 9/2011 | Cheng et al. |
| 2011/0218555 A1 | 9/2011 | Huitema |
| 2011/0218556 A1 | 9/2011 | Nguyen et al. |
| 2011/0224696 A1 | 9/2011 | Huitema et al. |
| 2011/0224700 A1 | 9/2011 | Schmidt et al. |
| 2011/0224701 A1 | 9/2011 | Menn |
| 2011/0230900 A1 | 9/2011 | Sarradon |
| 2011/0245847 A1 | 10/2011 | Menn |
| 2011/0245848 A1 | 10/2011 | Rosenberg et al. |
| 2011/0251608 A1* | 10/2011 | Timm et al. ............... 606/41 |

(56) References Cited

U.S. PATENT DOCUMENTS

| | | | |
|---|---|---|---|
| 2011/0295290 A1 | 12/2011 | Whitfield | |
| 2011/0313437 A1 | 12/2011 | Yeh | |
| 2012/0029533 A1 | 2/2012 | Whitfield et al. | |
| 2012/0029534 A1 | 2/2012 | Whitfield | |
| 2012/0041455 A1 | 2/2012 | Martinez | |
| 2012/0042497 A1 | 2/2012 | Zergiebel | |
| 2012/0046671 A1 | 2/2012 | Matsuoka et al. | |
| 2012/0059394 A1 | 3/2012 | Brenner et al. | |
| 2012/0065647 A1 | 3/2012 | Litscher et al. | |
| 2012/0109158 A1 | 5/2012 | Zammataro | |
| 2012/0116419 A1* | 5/2012 | Sigmon, Jr. | 606/142 |
| 2012/0116420 A1 | 5/2012 | Sorrentino | |
| 2012/0123446 A1 | 5/2012 | Aranyi | |
| 2012/0197269 A1 | 8/2012 | Zammataro | |
| 2012/0265220 A1 | 10/2012 | Menn | |
| 2012/0277765 A1 | 11/2012 | Zammataro | |
| 2012/0330326 A1 | 12/2012 | Creston | |
| 2013/0110135 A1 | 5/2013 | Whitfield | |
| 2013/0131697 A1 | 5/2013 | Hartoumbekis | |
| 2013/0165951 A1 | 6/2013 | Blake, III | |
| 2013/0165952 A1 | 6/2013 | Whitfield | |
| 2013/0172910 A1 | 7/2013 | Malkowski | |
| 2013/0172911 A1 | 7/2013 | Rockrohr | |
| 2013/0172912 A1 | 7/2013 | Whitfield | |
| 2013/0190779 A1 | 7/2013 | Whitfield | |
| 2013/0190780 A1 | 7/2013 | Whitfield | |
| 2013/0253541 A1 | 9/2013 | Zergiebel | |
| 2013/0274767 A1 | 10/2013 | Sorrentino | |
| 2013/0289583 A1 | 10/2013 | Zergiebel | |
| 2013/0296891 A1 | 11/2013 | Hartoumbekis | |
| 2013/0296892 A1 | 11/2013 | Sorrentino | |
| 2013/0310849 A1 | 11/2013 | Malkowski | |
| 2013/0325040 A1 | 12/2013 | Zammataro | |
| 2014/0039526 A1 | 2/2014 | Malkowski | |
| 2014/0052157 A1 | 2/2014 | Whitfield | |
| 2014/0058412 A1 | 2/2014 | Aranyi | |
| 2014/0194903 A1 | 7/2014 | Malkowski et al. | |
| 2014/0207156 A1 | 7/2014 | Malkowski | |
| 2014/0316441 A1 | 10/2014 | Zergiebel et al. | |
| 2014/0330291 A1 | 11/2014 | Whitfield et al. | |
| 2015/0005790 A1 | 1/2015 | Whitfield et al. | |
| 2015/0032131 A1 | 1/2015 | Sorrentino et al. | |
| 2015/0066057 A1 | 3/2015 | Rockrohr et al. | |
| 2015/0080916 A1 | 3/2015 | Aranyi et al. | |
| 2015/0127022 A1 | 5/2015 | Whitfield et al. | |

FOREIGN PATENT DOCUMENTS

| | | |
|---|---|---|
| CN | 101664329 A | 3/2010 |
| DE | 20 2009 006113 | 7/2009 |
| EP | 0 073 655 A1 | 3/1983 |
| EP | 0 085 931 A2 | 8/1983 |
| EP | 0 086 721 | 8/1983 |
| EP | 0 089 737 A1 | 9/1983 |
| EP | 0 092 300 A1 | 10/1983 |
| EP | 0 324 166 A2 | 7/1989 |
| EP | 0 392 750 A1 | 10/1990 |
| EP | 0 409 569 A1 | 1/1991 |
| EP | 0 569 223 | 11/1993 |
| EP | 0 594 003 | 4/1994 |
| EP | 0 598 529 A2 | 5/1994 |
| EP | 0 685 204 A1 | 12/1995 |
| EP | 0 732 078 A2 | 9/1996 |
| EP | 0 755 655 A2 | 1/1997 |
| EP | 0 769 274 | 4/1997 |
| EP | 0 769 274 A1 | 4/1997 |
| EP | 0 769 275 A1 | 4/1997 |
| EP | 0 834 286 A1 | 4/1998 |
| EP | 1 317 906 A1 | 6/2003 |
| EP | 1 609 427 A1 | 12/2005 |
| EP | 1 712 137 | 10/2006 |
| EP | 1 712 191 A2 | 10/2006 |
| EP | 1 757 236 | 2/2007 |
| EP | 1 813 199 A1 | 8/2007 |
| EP | 1 894 531 A2 | 3/2008 |
| EP | 1 908 423 | 4/2008 |
| EP | 1 908 423 A2 | 4/2008 |
| EP | 1 913 881 A1 | 4/2008 |
| EP | 1 939 231 A1 | 7/2008 |
| EP | 2 229 895 A1 | 9/2010 |
| EP | 2 332 471 | 6/2011 |
| EP | 2 412 318 A2 | 2/2012 |
| GB | 2073022 A | 10/1981 |
| JP | 10-118083 A | 5/1998 |
| JP | 2003 033361 A | 2/2003 |
| JP | 2006-501954 A | 1/2006 |
| JP | 2006-154230 A | 6/2006 |
| JP | 2006-209948 A | 8/2006 |
| JP | 2006-277221 A | 10/2006 |
| JP | 2007-250843 A | 9/2007 |
| JP | 2008-017876 A | 1/2008 |
| JP | 2008-047498 A | 2/2008 |
| JP | 2008-055165 A | 3/2008 |
| JP | 2008-515550 A | 5/2008 |
| JP | 2009-198991 A | 9/2009 |
| JP | 54-99386 B2 | 5/2014 |
| WO | WO 01/66001 | 9/2001 |
| WO | WO 01/67965 | 9/2001 |
| WO | WO 03/086207 | 10/2003 |
| WO | WO 03/092473 | 11/2003 |
| WO | 2004-032762 A1 | 4/2004 |
| WO | WO 2005/091457 A1 | 9/2005 |
| WO | WO 2006/042076 | 4/2006 |
| WO | WO 2006/042076 A2 | 4/2006 |
| WO | WO 2006/042084 A2 | 4/2006 |
| WO | WO 2006/042110 | 4/2006 |
| WO | WO 2006/042110 A2 | 4/2006 |
| WO | WO 2006/042141 | 4/2006 |
| WO | WO 2006/135479 | 12/2006 |
| WO | WO 2008/118928 | 10/2008 |
| WO | WO 2008/118928 A2 | 10/2008 |
| WO | WO 2008/127968 | 10/2008 |
| WO | WO 2008/127968 A2 | 10/2008 |

OTHER PUBLICATIONS

Extended European Search Report corresponding to EP 14 15 1673.2, completed Apr. 25, 2014 and mailed May 8, 2014; (8 pp).

Extended European Search Report corresponding to EP 12 19 8745.7, completed Mar. 19, 2013 and mailed Apr. 11, 2013; (8 pp).

Extended European Search Report corresponding to EP 12 15 2989.5, completed Apr. 9, 2013 and mailed Apr. 18, 2013; (9 pp).

Extended European Search Report corresponding to EP 08 73 2820.9, completed Jul. 2, 2013 and mailed Jul. 9, 2013; (10 pp).

Extended European Search Report corresponding to EP 12 19 1706.6, completed Dec. 19, 2012 and mailed jan. 8, 2013; (6 pp).

Extended European Search Report corresponding to EP 13 17 2008.8, completed Aug. 14, 2013 and mailed Aug. 28, 2013; (8 pp).

Extended European Search Report corresponding to EP 13 16 6382.5, completed Nov. 19, 2013 and mailed Nov. 28, 2013; (8 pp).

Extended European Search Report corresponding to EP 11 25 0194.5, completed Nov. 25, 2013 and mailed Dec. 3, 2013; (8 pp).

Extended European Search Report corresponding to EP 10 25 1798.4, completed Dec. 12, 2013 and mailed Jan. 2, 2014; (9 pp).

The extended European Search Report corresponding to European Application No. EP 07 25 3905.9, completed Jan. 29, 2008; mailed Feb. 7, 2008; (7 Pages).

The partial European Search Report corresponding to European Application No. EP 07 25 3807.7, completed Jul. 23, 2008; mailed Aug. 1, 2008; (3 pages).

International Search Report corresponding to International Application No. PCT/US08/58185, completed Sep. 4, 2008; mailed Sep. 9, 2008; (2 Pages).

The International Search Report corresponding to International Application No. PCT/US08/59859, completed Sep. 14, 2008; mailed Sep. 18, 2008; (2 Pages).

The extended European Search Report corresponding to European Application No. EP 07 25 3807.7, completed Nov. 7, 2008; mailed Nov. 26, 2008; (11 Pages).

(56) References Cited

OTHER PUBLICATIONS

The extended European Search Report corresponding to European Application No. EP 09 25 2049.3, completed Dec. 11, 2009; mailed Jan. 12, 2010; (3 Pages).
The extended European Search Report corresponding to European Application No. EP 09 25 2050.1, completed Dec. 23, 2009; mailed Jan. 21, 2010; (3 Pages).
The extended European Search Report corresponding to European Application No. EP 09 25 2051.9, completed Dec. 21, 2009; mailed Jan. 28, 2010; (3 Pages).
The extended European Search Report corresponding to European Application No. EP 09 25 2052.7, completed Nov. 16, 2009; mailed Nov. 24, 2009; (3 Pages).
The extended European Search Report corresponding to European Application No. EP 09 25 2053.5, completed Nov. 24, 2009; mailed Dec. 1, 2009; (3 Pages).
The extended European Search Report corresponding to European Application No. EP 09 25 2054.3, completed Jan. 7, 2010; mailed Jan. 22, 2010; (3 Pages).
The extended European Search Report corresponding to European Application No. EP 09 25 2056.8, completed Jan. 8, 2010; mailed Feb. 5, 2010; (3 Pages).
The extended European Search Report corresponding to European Application No. EP 10 25 0497.4, completed May 4, 2010; mailed May 12, 2010; (6 Pages).
The extended European Search Report corresponding to European Application No. EP 10 25 2079.8, completed Mar. 8, 2011; mailed Mar. 17, 2011; (3 Pages).
The European Search Report corresponding to European Application No. EP 05 81 0218.7, completed Apr. 18, 2011; mailed May 20, 2011; (3 pages).
The European Search Report corresponding to European Application No. EP 05 80 7612.6, completed May 2, 2011; mailed May 20, 2011; (3 pages).
The extended European Search Report corresponding to European Application No. EP 10 25 1737.2, completed May 9, 2011; mailed May 20, 2011; (4 pages).
The extended European Search Report corresponding to European Application No. EP 11 00 2681.2, completed May 31, 2011; mailed Jun. 10, 2011; (3 Pages).
The extended European Search Report corresponding to European Application No. EP 11 25 0214.1, completed May 25, 2011; mailed Jun. 1, 2011; (3 Pages).
The European Search Report corresponding to European Application No. EP 05 80 2686.5, completed Jan. 9, 2012; mailed Jan. 18, 2012; (3 Pages).
The extended European Search Report corresponding to European Application No. EP 12 15 1313.9, completed Mar. 20, 2012 and mailed Apr. 12, 2012; (5 Pages).
The extended European Search Report corresponding to European Application No. EP 12 16 1291.5, completed Apr. 24, 2012 and mailed May 4, 2012; (5 Pages).
The extended European Search Report corresponding to European Application No. EP 12 16 2288.0, completed Jun. 4, 2012 and mailed Jul. 7, 2012; (6 Pages).
The extended European Search Report corresponding to European Application No. EP 12 16 5891.8, completed Jun. 12, 2012 and mailed Jun. 20, 2012; (6 Pages).
The extended European Search Report corresponding to European Application No. EP 12 16 4955.2, completed Aug. 23, 2012 and mailed Sep. 4, 2012; (5 Pages).
The extended European Search Report corresponding to European Application No. EP 11 25 0754.6, completed Oct. 22, 2012 and mailed Oct. 31, 2012; (6 Pages).
The extended European Search Report corresponding to European Application No. EP 12 18 6448.2, completed Nov. 28, 2012 and mailed Dec. 10, 2012; (6 Pages).
The extended European Search Report corresponding to European Application No. EP 12 18 6401.1, completed Nov. 22, 2012 and mailed Nov. 30, 2012; (7 Pages).
The extended European Search Report corresponding to European Application No. EP 12 19 1706.6, completed Dec. 19, 2012 and mailed Jan. 8, 2013; (6 Pages).
"Salute II Disposable Fixation Device", Technique Guide—Laparoscopic and Open Inguinal and Ventral Hernia Repair; Davol, A Bard Company, 2006; (7 Pages).
Japanese Office Action corresponding to JP 2011-160130 mailed Dec. 1, 2014.
Chinese Office Action corresponding to CN 201210015011.8 issued Jan. 4, 2015.
Japanese Office Action corresponding to JP 2011-160126 mailed Jan. 9, 2015.
Japanese Office Action corresponding to JP 2011-184521 mailed Jan. 15, 2015.
Extended European Search Report corresponding to 14 18 2236.1 dated Jan. 20, 2015.
Chinese Office Action corresponding to CN 201110201736.1 issued Feb. 9, 2015.
Extended European Search Report corresponding to EP 14 16 1540.1 dated Feb. 27, 2015.
Australian Office Action corresponding to AU 2010226985 issued Mar. 31, 2015.
Australian Office Action corresponding to AU 2013211526 issued Apr. 6, 2015.
Australian Office Action corresponding to AU 2011211463 issued Apr. 13, 2015.
Australian Office Action corresponding to AU 2013254887 issued Apr. 14, 2015.
Japanese Office Action corresponding to JP 2013-225272 mailed May 1, 2015.
European Office Action corresponding to EP 12 152 989.5 dated May 4, 2015.
Australian Office Action corresponding to AU 2009212759 issued May 7, 2015.
Japanese Office Action corresponding to JP 2013-229070 mailed May 8, 2015.
Japanese Office Action corresponding to JP 2013-229996 mailed May 8, 2015.
Japanese Office Action corresponding to JP 2014-190735 dated May 27, 2015; no English translation attached—unavailable.
Chinese Office Action dated Nov. 2, 2015 in corresponding Chinese Application No. 201210555570.8.
European Search Report EP12197813 dated Mar. 7, 2016.

* cited by examiner

JAW CLOSURE MECHANISM FOR A SURGICAL CLIP APPLIER

CROSS REFERENCE TO RELATED APPLICATION

The present application claims the benefit of and priority to U.S. Provisional Application Ser. No. 61/577,130, filed on Dec. 19, 2011, the entire contents of which are incorporated herein by reference.

BACKGROUND

1. Technical Field

The present disclosure relates to surgical instruments. More particularly, the present disclosure relates to a jaw closure mechanism for use in a surgical clip applier.

2. Description of Related Art

Surgical staplers and clip appliers are known in the art and are used for a number of distinct and useful surgical procedures. In the case of a laparoscopic surgical procedure, access to the interior of an abdomen is achieved through narrow tubes or cannulas inserted through a small entrance incision in the skin. Minimally invasive procedures performed elsewhere in the body are often generally referred to as endoscopic procedures. Typically, a tube or cannula device is extended into the patient's body through the entrance incision to provide an access port. The port allows the surgeon to insert a number of different surgical instruments therethrough using a trocar and for performing surgical procedures far removed from the incision.

During a majority of these procedures, the surgeon must often terminate the flow of blood or another fluid through one or more vessels. The surgeon will often apply a surgical clip to a blood vessel or another duct to prevent the flow of body fluids therethrough during the procedure. An endoscopic clip applier is known in the art for applying a single clip or a series of clips during a surgical procedure. Such clips are typically fabricated from a biocompatible material and are usually compressed over a vessel. Once applied to the vessel, the compressed clip terminates the flow of fluid therethrough. Open surgical clip appliers operate in a similar fashion.

Endoscopic clip appliers that are able to apply multiple clips in endoscopic or laparoscopic procedures during a single entry into the body cavity are described in commonly-assigned U.S. Pat. Nos. 5,084,057 and 5,100,420 to Green et al., which are both incorporated by reference in their entirety. Another multiple endoscopic clip applier is disclosed in commonly-assigned U.S. Pat. No. 5,607,436 by Pratt et al., the contents of which is also hereby incorporated by reference herein in its entirety. These devices are typically, though not necessarily, used during a single surgical procedure. U.S. patent application Ser. No. 08/515,341 now U.S. Pat. No. 5,695,502 to Pier et al., the disclosure of which is hereby incorporated by reference herein, discloses a resterilizable surgical clip applier. The clip applier advances and forms multiple clips during a single insertion into the body cavity. This resterilizable clip applier is configured to receive and cooperate with an interchangeable clip magazine so as to advance and form multiple clips during a single entry into a body cavity.

One significant design goal in the manufacture of clip appliers is to provide a clip applier that maximizes the jaw closure force imparted to the jaws to help ensure complete and proper formation of the clip onto the body tissue or vessel while also minimizing the drive force applied by the user to actuate the jaws so as to permit relatively easy actuation of the jaws and to inhibit fatigue during the course of a surgical procedure. In particular, it would be desirable to provide a clip applier having a jaw closure mechanism configured to maximize the ratio of jaw closure force to drive force.

SUMMARY

In accordance with the present disclosure, a jaw closure mechanism for use in a surgical clip applier having first and second jaws movable relative to one another between a spaced-apart position and an approximated position to form a surgical clip about tissue is provided. The jaw closure mechanism includes first and second eccentric wheels and a cable disposed about the first and second eccentric wheels. The first and second eccentric are wheels rotatably coupled to the respective first and second jaws. Each of the first and second eccentric wheels includes a center and a pivot point that is offset relative to the center. A cable is disposed about each of the first and second eccentric wheels. More specifically, the cable is engaged to the first eccentric wheel at a first engagement point and to the second eccentric wheel at a second engagement point such that, upon application of a drive force to the cable, the first and second eccentric wheels are rotated and displaced relative to the respective first and second jaws from a first position to a second position to urge the first and second jaws from the spaced-apart position to the approximated position.

In the first position, the center, the pivot point, and/or the engagement point of each of the first and second eccentric wheels may be axially aligned with one another. Additionally or alternatively, in the second position the center, the pivot point, and the engagement point of each of the first and second eccentric wheels may be angled with respect to one another.

In embodiments, the jaw closure mechanism further includes a drive bar coupled to the cable and configured to apply the drive force to the cable. More specifically, the drive bar may be selectively translatable between a more distal position and a more proximal position to apply the drive force to the cable.

In embodiments, upon translation of the drive bar from the more distal position to the more proximal position, the cable applies an oblique force to each of the first and second eccentric wheels. Further, the oblique force applied to each of the first and second eccentric wheels may urge the first and second eccentric wheels to displace and rotate relative to the respective first and second jaws, thereby applying a jaw closure force to the first and second jaws to move the first and second jaws from the spaced-apart position to the approximated position.

In embodiments, the jaw closure force is a product of the drive force and a force transformation multiplier. The force transformation multiplier is inversely proportional to an angle defined between a direction of the oblique force and a direction of the jaw closure force.

In embodiments, the rotation and displacement of the first and second eccentric wheels minimizes the angle defined between the direction of the oblique force and the direction of the jaw closure force as the first and second eccentric wheels are transitioned from the first position to the second position, thereby maximizing the force transformation multiplier.

In embodiments, the jaw closure mechanism is releasably engagable with the first and second jaws.

A surgical clip applier is also provided in accordance with the present disclosure. The surgical clip applier includes a jaw assembly and a jaw closure mechanism. The jaw assembly includes first and second jaws movable between a spaced-apart position and an approximated position to apply a surgical clip to tissue. The jaw closure mechanism includes first and second eccentric wheels rotatably coupled to the respective first and second jaws and a cable disposed about each of the first and second eccentric wheels. The cable is engaged to the first eccentric wheel at a first engagement point and to the second eccentric wheel at a second engagement point such that, upon application of a longitudinal drive force to the cable, the cable applies an oblique force to each of the first and second eccentric wheels to rotate and displace the first and second eccentric wheels, thereby applying a transverse jaw closure force to the first and second jaws to urge the first and second jaws from the spaced-apart position to the approximated position.

In embodiments, the surgical clip applier further includes a drive assembly having a drive bar that is coupled to the cable. The drive bar is selectively translatable between a more distal position and a more proximal position to apply the longitudinal drive force to the cable.

In embodiments, the surgical clip applier further includes a trigger assembly that is operably coupled to the drive assembly. The trigger assembly is selectively actuatable to translate the drive bar between the more distal position and the more proximal position.

In embodiments, the transverse jaw closure force is a product of the longitudinal drive force and a force transformation multiplier. The force transformation multiplier being inversely proportional to an angle defined between a direction of the oblique force and a direction of the transverse jaw closure force. In such embodiments, the rotation and displacement of the first and second eccentric wheels may be configured to minimize the angle defined between the direction of the oblique force and the direction of the transverse jaw closure force as the first and second jaws are urged from the spaced-apart position to the approximated position, thereby maximizing the force transformation multiplier.

In embodiments, the jaw closure mechanism is releasably engagable with jaw assembly.

A method of transforming a longitudinal drive force into a transverse jaw closure force in a surgical clip applier having first and second jaws movable relative to one another between a spaced-apart position and an approximated position to form a surgical clip about tissue is also provided in accordance with the present disclosure. The method includes applying a longitudinal drive force, transforming the longitudinal drive force into a transverse jaw closure force, applying the transverse jaw closure force to the first and second jaws to move the first and second jaws relative to one another between the spaced-apart position and the approximated position to form the surgical clip about tissue, and minimizing an angle defined between a direction of the oblique force and a direction of the transverse jaw closure force while the transverse jaw closure force is being applied to the first and second jaws to thereby maximize a ratio of jaw closure force to longitudinal drive force.

BRIEF DESCRIPTION OF THE DRAWINGS

Various embodiments of the present disclosure are described herein with reference to the drawings wherein:

FIG. 3 is an enlarged, perspective view of a jaw assembly configured for use with the clip appliers of FIGS. 1 and 2;

DETAILED DESCRIPTION

Figure 1:
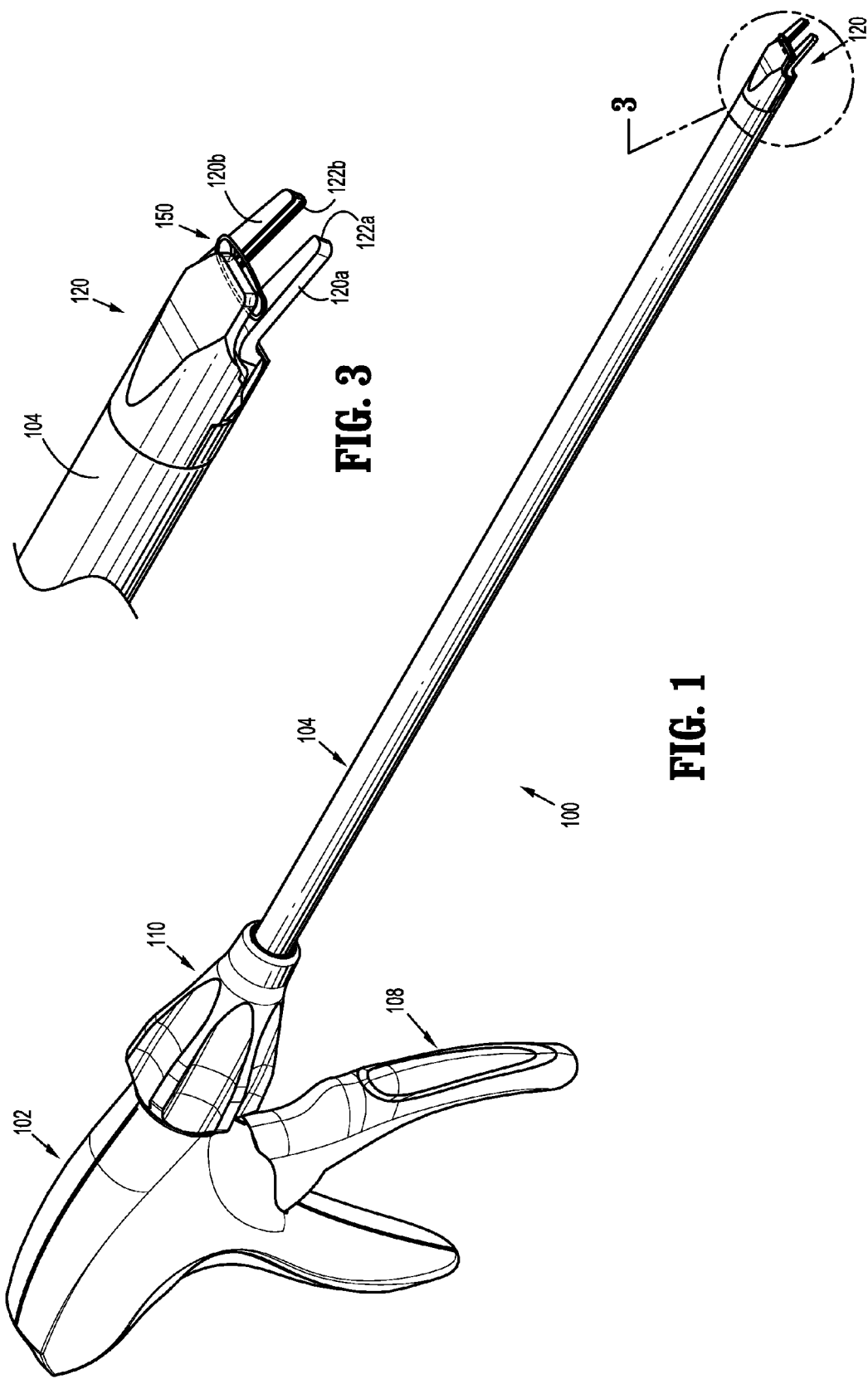
FIG. 1 is a perspective view of an endoscopic surgical clip applier according to the present disclosure.

Embodiments of a jaw closure mechanism for a surgical clip applier in accordance with the present disclosure will now be described in detail with reference to the drawing figures wherein like reference numerals identify similar or identical structural elements. As shown in the drawings and described throughout the following description, as is traditional when referring to relative positioning on a surgical instrument, the term "proximal" refers to the end which is closer to the user and the term "distal" refers to the end which is further away from the user.

Referring briefly to FIG. 1, an endoscopic surgical clip applier is shown generally identified by reference numeral 100. Surgical clip applier 100 generally includes a handle assembly 102 and an endoscopic portion including a shaft assembly 104 extending distally from handle assembly 102 and having a jaw assembly 120 disposed at a distal end thereof. Handle assembly 102 further includes a rotating assembly 110 rotatable in either direction to effect corresponding rotation of jaw assembly 120, and a trigger assembly 108 that is selectively squeezable to actuate jaw assembly 120 to form a surgical clip "C" (FIGS. 4A-4B) about tissue. A stack of surgical clips is typically loaded and/or retained within shaft assembly 104 in a manner so as to slide therewithin and/or therealong, ultimately such that a plurality of surgical clips "C" (FIGS. 4A-4B) may be sequentially provided to jaw assembly 120 for formation about tissue. A complete description of the inner-workings and operation of surgical clip applier 100 can be found in commonly-assigned U.S. patent application Ser. No. 12/055,446 to Whitfield et. al. (U.S. Patent Application Publication No. 2008/0243145), filed on Mar. 26, 2008, the entire contents of which are hereby incorporated by reference herein.

Figure 2:
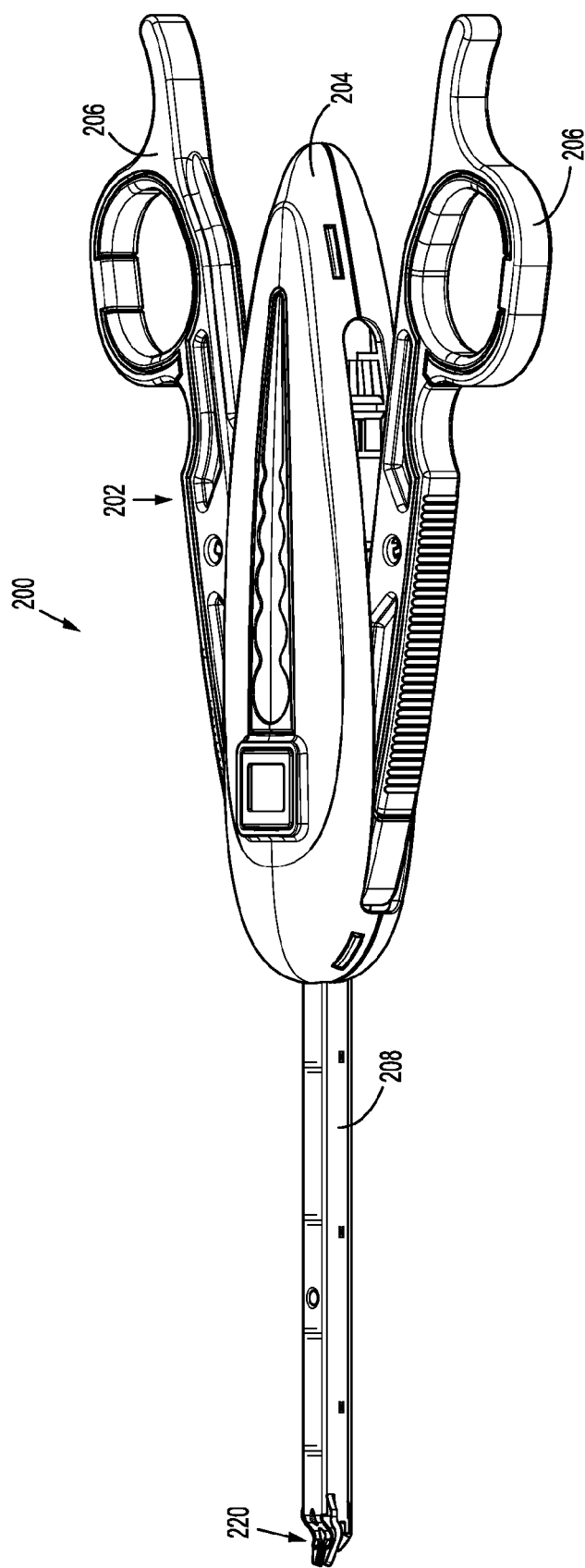
FIG. 2 is a top, perspective view of an open surgical clip applier according to the present disclosure.

Referring briefly to FIG. 2, an open surgical clip applier is shown generally identified by reference numeral 200. Surgical clip applier 200 generally includes a handle assembly 202 including a housing 204 and a shaft assembly 208 extending distally from housing 204 and including a jaw assembly 220 disposed at a distal end thereof. Housing 204 further includes a pair of handles 206 pivotally coupled thereto and extending outwardly from housing 204. Handles 206 are selectively squeezable to actuate jaw assembly 220 to form a surgical clip "C" (FIGS. 4A-4B) about tissue. A stack of surgical clips is typically loaded and/or retained within shaft assembly 208 in a manner so as to slide therewithin and/or therealong, ultimately such that a plurality of surgical clips "C" (FIGS. 4A-4B) may be sequentially provided to jaw assembly 220 for formation about tissue. A complete description of the inner-workings and operation of surgical clip applier 200 can be found in commonly-assigned U.S. patent application Ser. No. 12/540,475 to Zergiebel (U.S. Patent Application Publication No. 2010/0049216), filed on Aug. 13, 2009, the entire contents of which are hereby incorporated by reference herein.

Turning now to FIG. 3, jaw assembly 120 of surgical clip applier 100 (FIG. 1) is shown, although jaw assembly 120 may alternatively be configured for use with surgical clip applier 200 (FIG. 2), or any other suitable surgical clip applier. However, for purposes of simplicity and consistency, jaw assembly 120 will be described in conjunction with surgical clip applier 100 only.

Referring to FIG. 3, in conjunction with FIG. 1, jaw assembly 120 is mounted in the distal end of shaft assembly 104 such that jaws 120a, 120b are longitudinally stationary relative thereto. Jaws 120a and 120b of jaw assembly 120 each define a recess 122a, 122b on an inwardly facing surface thereof that is configured to guide passage of a surgical clip "C" (FIGS. 4A-4B) therethrough. Once the surgical clip "C" (FIGS. 4A-4B) is positioned between jaws 120a, 120b, trigger assembly 108 may be actuated to approximate jaws 120a, 120b relative to one another to form the surgical clip "C" (FIGS. 4A-4B) about tissue. More specifically, a jaw closure mechanism 150 is coupled to each of jaws 120a, 120b of jaw assembly 120 and to drive bar 140 (FIGS. 4A-4B) such that, upon actuation of trigger assembly 108 to translate drive bar 140 (FIGS. 4A-4B) proximally, jaws 120a, 120b are moved from a first, spaced-apart position (FIG. 4A) to a second, approximated position (FIG. 4B) to form the surgical clip "C" (FIGS. 4A-4B) disposed therebetween about tissue. Further, jaws 120a, 120b may be biased towards the first, spaced-apart position (FIG. 4A) such that jaws 120a, 120b are returned to the first, spaced-apart position (FIG. 4A) upon release of trigger assembly 108. Jaw closure mechanism 150 is described in greater detail below with reference to FIGS. 4A-5B.

Turning now to FIGS. 4A-4B and 5A-5B, jaw closure mechanism 150 is described. Jaw closure mechanism 150 generally includes a pair of discs, or wheels 152, 154 each of which is rotatably mounted on one of the jaws 120a, 120b, respectively, and a belt, or cable 156 looped about both of the wheels 152, 154. More specifically, each jaw 120a, 120b includes a pivot post 123a, 123b extending upwardly therefrom that is received within an aperture 153, 155 defined through wheels 152, 154, respectively, to rotatably couple wheels 152, 154 to jaws 120a, 120b, respectively. However, although pivot posts 123a, 123b are shown extending upwardly from respective jaws 120a, 120b, it is envisioned that pivot posts 123a, 123b may be positioned to extend downwardly from jaws 120a, 120b, may extend through a cavity defined within jaws 120a, 120b, or may otherwise be positioned to rotatably support wheels 152, 154 thereon.

Continuing with reference to FIGS. 4A-4B and 5A-5B, apertures 153, 155, defined through wheels 152, 154, respectively, are eccentrically positioned relative to wheels 152, 154. That is, apertures 153, 155 are not defined through the center "X" of wheels 152, 154 but, rather, are offset from the center "X" of wheels 152, 152, respectively, a distance "$d_1$." Such a feature, as will be described below, increases the ratio of jaw closure force (e.g., the force acting normal to jaws 120a, 120b to urge jaws 120a, 120b from the first, spaced-apart position (FIGS. 4A and 5A) to the second, approximated position (FIGS. 4B and 5B)) to drive force (e.g., the force acting on drive bar 140 to translate drive bar 140 proximally).

As mentioned above, cable 156 is looped about both of the wheels 152, 154. More specifically, cable 156 is looped about wheels 152, 154 and is fixedly engaged to the outer periphery of each wheel 152, 154 at engagement points "$E_1$," "$E_2$," respectively. Cable 156 may be engaged to wheels 152, 154 in any suitable fashion, e.g., pinching, welding, pin-aperture engagement, etc. Further, cable 156 may be formed from a rigid, semi-rigid, or flexible material. Cable 156 may also be disposed about wheels 152, 154 in a tensioned state such that cable 156 biases jaws 120a, 120b towards the spaced-apart position.

Figure 4A:
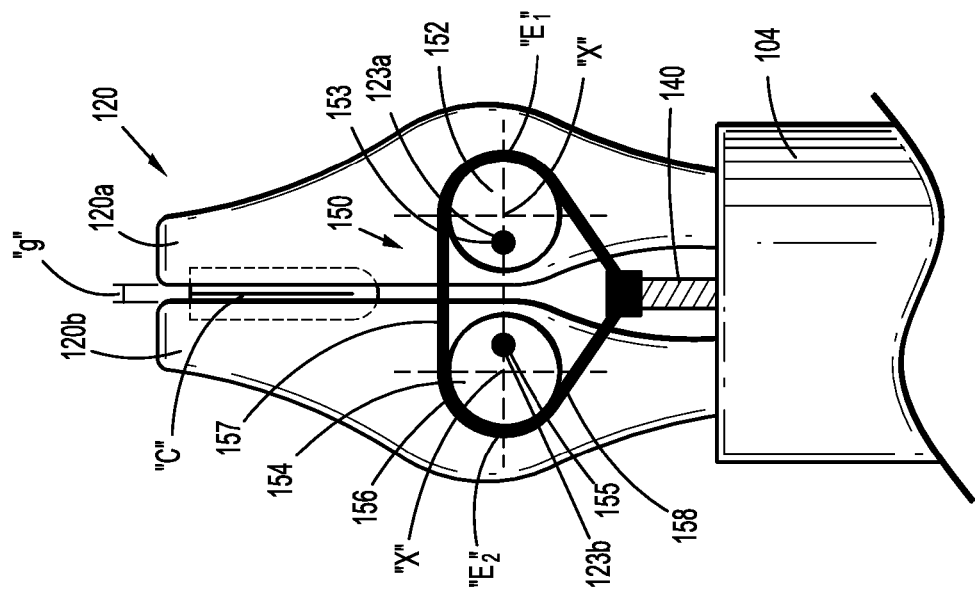
FIG. 4A is a top view of the jaw assembly of FIG. 3 shown in a first position.
Figure 4B:
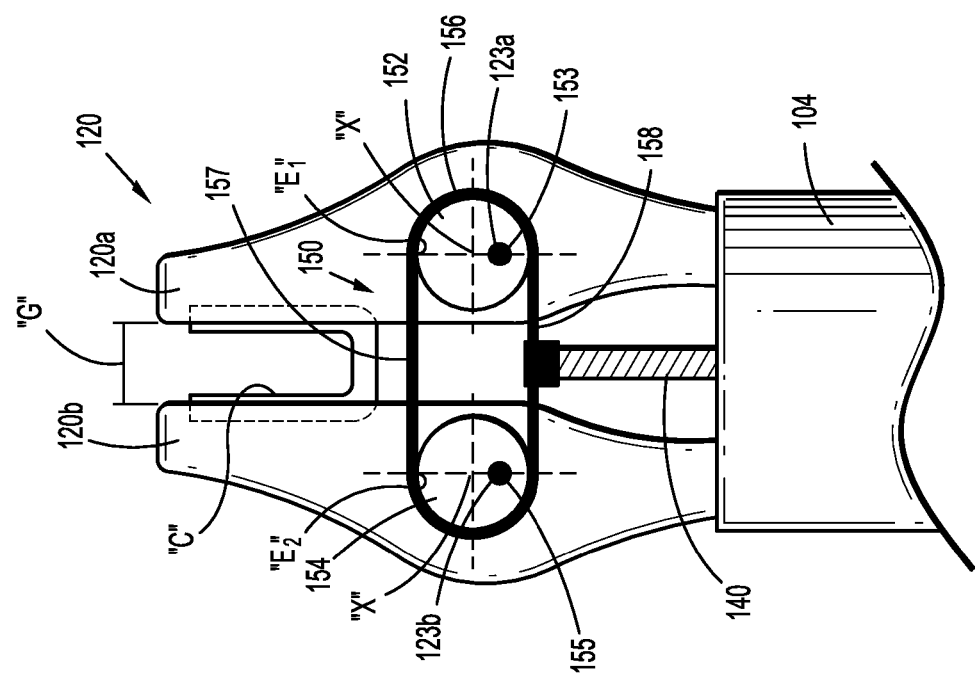
FIG. 4B is a top view of the jaw assembly of FIG. 3 shown in a second position.

As best shown in FIGS. 4A and 4B, cable 156 includes a distal segment 157 and a proximal segment 158, while the remainder of cable 156 is circumferentially disposed about a portion of either of wheels 152, 124. Distal segment 157 of cable 156 extends between wheels 152, 154 and, more particularly, between engagement points "$E_1$," "$E_2$" of wheels 152, 154, respectively, towards the distal end of jaw closure mechanism 150. As can be appreciated, since cable 156 is fixed at engagement points "$E_1$" and "$E_2$," the distance between engagement points "$E_1$" and "$E_2$" along cable 156 is a fixed distance "$d_2$." Proximal segment 158 of cable 156, on the other hand, extends between wheels 152, 154 towards the proximal end of jaw closure mechanism 150.

Figure 5A:
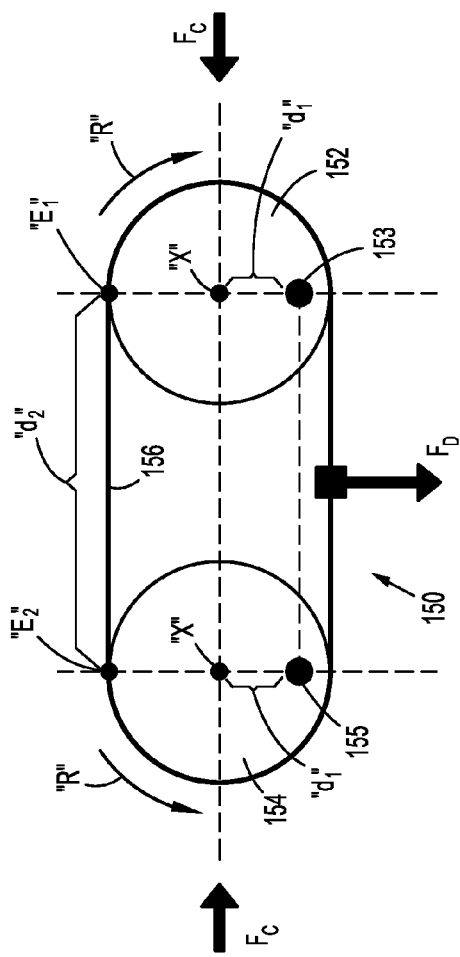
FIG. 5A is a schematic illustration of a jaw closure mechanism of the jaw assembly of FIG. 3, wherein the jaw closure mechanism is in a first position.
Figure 5B:
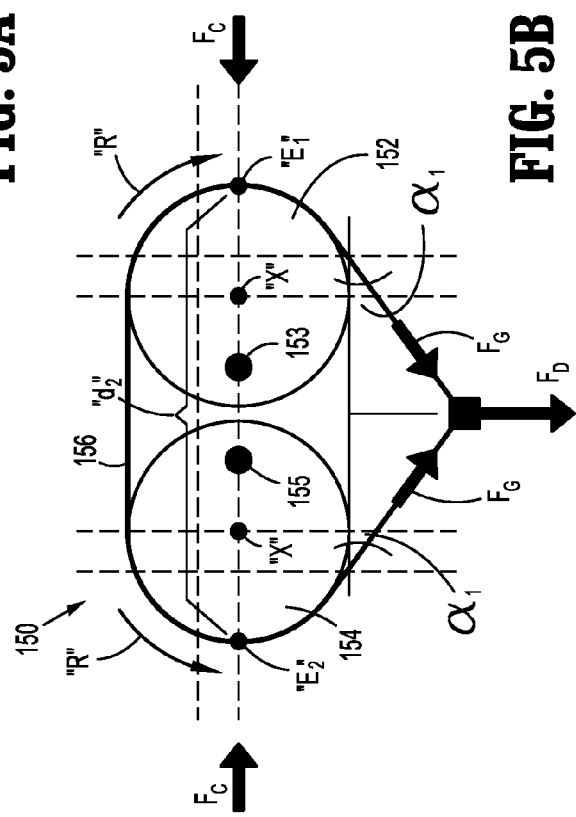
FIG. 5B is a schematic illustration of the jaw closure mechanism of the jaw assembly of FIG. 3, wherein the jaw closure mechanism is in a second position.

Drive bar 140 is engaged to proximal segment 158 of cable 156 in any suitable fashion, e.g., pinching, welding, pin-aperture engagement, etc., and extends proximally therefrom, ultimately coupling to a drive mechanism (not shown) disposed within handle assembly 102 (FIG. 1) that, upon actuation of trigger assembly 108 (FIG. 1), cooperate to translate drive bar 140 proximally relative to jaw assembly 120 to move jaws 120a, 120b between the first, spaced-apart position (FIGS. 4A and 5A) and the second, approximated position (FIGS. 4B and 5B). More particularly, as will be described in greater detail below, proximal translation of drive bar 140 pulls proximal segment 158 of cable 156 proximally such that wheels 152, 154 are rotated about pivot posts 123a, 123b, respectively, and, ultimately such that jaws 120a, 120b are brought into approximation with one another.

Referring again to FIGS. 4A-4B and 5A-5B, the use and operation of jaw closure mechanism 150, including a more detailed description of the working components thereof, is described. Initially, as shown in FIGS. 4A and 5A, jaws 120a, 120b are disposed in the first, spaced-apart position. With jaws 120a, 120b in the first, spaced-apart position, drive bar 140 is in a more distal position and, accordingly, cable 156 is disposed in an at-rest position defining a generally oval-shaped configuration wherein distal and proximal segments 157, 158, respectively, of cable 156 are substantially parallel to one another in generally transverse orientation relative to jaws 120a, 120b. Further, in the initial position, engagement points "$E_1$" and "$E_2$" are distally spaced from and axially aligned with the center "X" of respective wheels 152, 154. Apertures 153, 155, through which posts 123a, 123b of jaws 120a, 120b, respectively, extend, are proximally spaced from and axially aligned with the center "X" of respective wheels 152, 154 as well as with the respective attachment point "$E_1$," "$E_2$" thereof.

Continuing with reference to FIGS. 4A and 5A, in this initial position, jaws 120a, 120b are spaced-apart a maximum distance "G," which is dependent at least on the length of cable 156, the distance "$d_2$" between engagement points "$E_1$" and "$E_2$," and the diameters of wheels 152, 154. Accordingly, cable 156 and wheels 152, 154 may be configured and/or dimensioned to define a specific maximum distance "G" therebetween, which may ultimately depend on the type, size, and/or shape of the surgical clip "C" to be applied to tissue, or on other factors. To this end, jaw closure mechanism 150 may be releasably engagable with jaw assembly 120, e.g., wheels 152, 154 may be coupled to posts 123a, 123b, respectively, such that an appropriately configured jaw closure mechanism 150 may be selected and engaged to jaw assembly 120 depending on the particular type, size, and/or shape of the surgical clip "C" to be applied, or on other factors.

Referring again to FIGS. 4A-4B and 5A-5B, upon actuation, e.g., upon actuation of trigger assembly 108 (FIG. 1), or prior thereto, e.g., upon release of trigger assembly 108 (FIG. 1) after a previous actuation, a surgical clip "C" is loaded into, or advanced between, jaws 120a, 120b. Next, with the surgical clip "C" disposed between jaws 120a, 120b, jaws 120a, 120b may be approximated relative to one another to form the surgical clip "C" about tissue (not shown). In order to approximate jaws 120a, 120b, the drive assembly (not shown) is activated, e.g., via actuation of trigger assembly 108 (FIG. 1), to translate, or pull, drive bar 140 proximally relative to jaw assembly 120. As drive bar 140 is pulled proximally, cable 156 and, in particular, proximal segment 158 of cable 156, is likewise pulled proximally due to the engagement between drive bar 140 and proximal segment 158 of cable 156.

As drive bar 140 is pulled proximally to similarly pull proximal segment 158 of cable 156 proximally, wheels 152, 154 are rotated about posts 123a, 123b of jaws 120a, 120b, respectively, in the direction of arrows "R" due to the engagement of cable 156 to wheels 152, 154 at respective engagement points "E₁" and "E₂." Rotation of wheels 152, 154 in the direction of arrows "R" not only rotates wheels 152, 154 relative to jaws 120a, 120b, but also displaces wheels 152, 154 relative to jaws 120a, 120b. More specifically, due to the eccentric positioning of apertures 153, 155 (i.e., the pivot points of wheels 152, 154) relative to the centers "X" of respective wheels 152, 154, rotation of wheels 152, 154 about posts 123a, 123b displaces wheels 152, 154 such that the centers "X" of wheels 152, 154, are moved in a generally outward and proximal direction relative to jaws 120a, 120b. As a result of this eccentric rotation of wheels 152, 154 and corresponding displacement of wheels 152, 154, jaws 120a, 120b are urged toward one another, i.e., toward the approximated position, to maintain the fixed distance "d₂" along cable 156 between engagement points "E₁" and "E₂."

With reference to FIGS. 4B and 5B, as drive bar 140 is pulled further proximally, wheels 152, 154 are rotated further in the direction of arrows "R" and are displaced further proximally and outwardly, such that jaws 120a, 120b are ultimately moved to the approximated position to form the surgical clip "C" disposed therebetween about tissue. In the approximated position, jaws 120a, 120b define a minimum gap distance "g" therebetween. The minimum gap distance "g" is dependent at least on the length of cable 156, the distance "d₂" between engagement points "E₁" and "E₂," the diameters of wheels 152, 154, and the distance "d₁" between the centers "X" of wheels 152, 154 and the pivot points, i.e., apertures 153, 155, respectively, thereof. Accordingly, a suitably configured jaw closure mechanism 150 may be selected to achieve a desired minimum gap distance "g" between jaws 120a, 120b in the approximated position. Further, in the approximated position, engagement points "E₁" and "E₂" may be longitudinally aligned with and transversely spaced from the center "X" of respective wheels 152, 154. Apertures 153, 155, through which posts 123a, 123b of jaws 120a, 120b, respectively, extend, may be longitudinally aligned with and transversely spaced from the center "X" of respective wheels 152, 154 and with engagement points "E₁" and "E₂."

Referring again to FIGS. 4A-4B and 5A-5B, once the surgical clip "C" has been formed about tissue, jaws 120a, 120b may be returned to the spaced-apart position, e.g., via release of trigger assembly 109 (FIG. 1). More specifically, in order to return jaws 120a, 120b back to the spaced-apart position, drive bar 140 is translated distally such that cable 156 is likewise translated distally (or is returned under bias) to permit wheels 152, 154 to rotate (in a direction opposite of arrows "R") and move back to the initial position shown in FIGS. 4A and 5A. As wheels 152, 154 are rotated and moved back to the initial position, jaws 120a, 120b are permitted to return under bias back to the spaced-apart position shown in FIGS. 4A and 5A. Thereafter, jaw assembly 120 may be removed from the surgical site or repositioned adjacent additional tissue structure(s) for applying one or more surgical clips "C" thereto.

Figure 6:
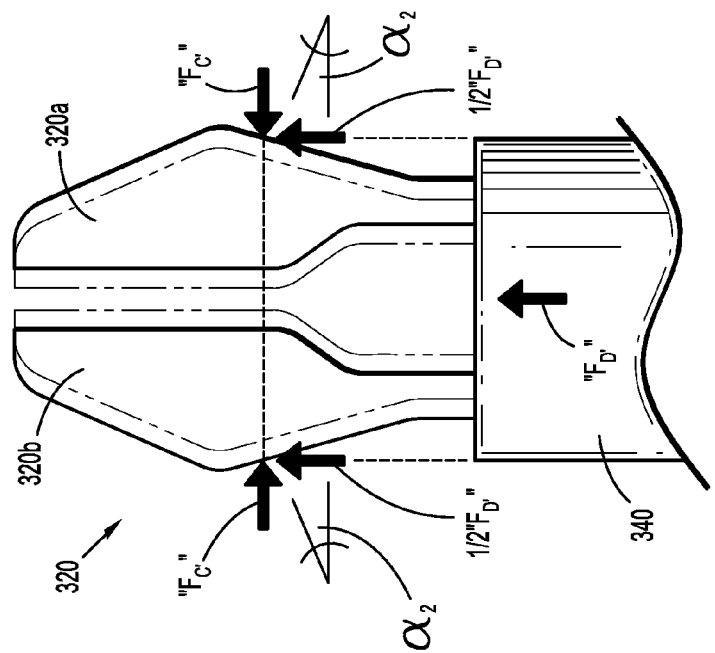
FIG. 6 is a schematic illustration of a prior art jaw assembly.

Turning now to FIGS. 5A-5B and 6, in conjunction with FIGS. 4A-4B, the improved mechanical advantage of the presently disclosed jaw closure mechanism 150, as compared to a prior art jaw assembly 320, is described. With respect to the presently disclosed jaw closure mechanism 150, as shown schematically in FIGS. 5A-5B, proximal translation of drive bar 140 exerts a proximal drive force "$F_D$" on cable 156 which, in turn, exerts a generally inward and proximal, i.e., an oblique force "$F_G$," on the portions of proximal segment 158 of cable 156 that extend between each of wheels 152, 154 and drive bar 140. As a result of the oblique forces "$F_G$" exerted on cable 156, wheels 152, 154 are rotated and displaced, thereby exerting a jaw closure force "$F_G$" on jaws 120a, 120b (i.e., a force normal to the opposed surfaces of jaws 120a, 120b) to urge jaws 120a, 120b towards the approximated position.

As can be appreciated, force vectors "$F_D$" and "$F_C$" are normal to one another, i.e., force vector "$F_D$" is applied in a longitudinal direction and force vector "$F_C$" is applied in a transverse direction, while force vectors "$F_C$" and "$F_G$" define an angle "$\alpha_1$," therebetween. Thus, the relationship between the drive force "$F_D$" and the jaw closure force "$F_C$" for jaw closure mechanism 150 can be represented as:

$$F_C = F_D * \frac{(1 + \cos\alpha_1)}{2\sin\alpha_1} \qquad \text{EQ 1:}$$

Equation 1 (EQ 1), above, can be simplified by rewriting the relationship between the drive force "$F_D$" and the jaw closure force "$F_C$" in terms of a force transformation multiplier "$T_1$," as either:

$$F_C = F_D * T_1 \qquad \text{EQ2:}$$

or, in the alternative, as:

$$F_D = \frac{F_C}{T_1} \qquad \text{EQ 3:}$$

where "$T_1$," the force transformation multiplier, is:

$$T_1 = \frac{(1 + \cos\alpha_1)}{2\sin\alpha_1} \qquad \text{EQ 4:}$$

Thus, the force transformation multiplier "$T_1$" is dependent on the angle "$\alpha_1$" between force vectors "$F_C$" and "$F_G$." As can be appreciated, it is desirable to maximize the force transformation multiplier "$T_1$" such that a greater jaw closure force "$F_C$" can be achieved relative to the drive force "$F_D$" applied, or, put another way, such that a relatively reduced drive force "$F_D$" can be applied to achieve the desired jaw closure force "$F_C$."

The following table, Table 1, indicates an approximation of the force transformation multiplier "$T_1$" for jaw closure mechanism 150 at various different angles "$\alpha_1$":

TABLE 1

| "α₁" (degrees) | 5 | 10 | 15 | 20 |
|---|---|---|---|---|
| "T₁" | 11.45 | 5.71 | 3.79 | 2.83 |

TABLE 2

| "α₂" (degrees) | 5 | 10 | 15 | 20 |
|---|---|---|---|---|
| "T₂" | 5.71 | 2.83 | 1.86 | 1.37 |

Further, according to Equation 4 (EQ 4), above, and the exemplary Table 1, above, minimizing the angle "$\alpha_1$" maximizes the force transformation multiplier "$T_1$." The presently disclosed jaw closure mechanism 150 takes advantage of this relationship in that jaw closure mechanism 150 minimizes the angle "$\alpha_1$" between force vectors "$F_C$" and "$F_G$." More specifically, due to the eccentric feature of wheels 152, 154, wheels 152, 154 are rotated and displaced relative to jaws 120a, 120b upon application of drive force "$F_D$" to cable 156 such that the angle "$\alpha_1$" is minimized as wheels 152, 154 are rotated. Thus, the eccentric features of wheels 152, 154 maximize the force transformation multiplier "$T_1$" and, accordingly, allow for greater jaw closure force "$F_C$" for a given drive force "$F_D$" (see Equation 2 (EQ 2), above) or, in the alternative, allow for the application of a reduced drive force "$F_D$" to achieve a desired jaw closure force "$F_C$" (see Equation 3 (EQ 3), above).

Turning now to FIG. 6, a prior art jaw assembly 320 is shown generally including first and second jaws 320a, 320b and a cam sleeve 340 that is translatable about and relative to jaws 320a, 320b to move jaws 320a, 320b between a spaced-apart position (as shown) and an approximated position (shown in phantom). In this configuration, the drive force "$F_D$" is applied in a longitudinal and distal direction and the jaw closure force "$F_C$" is applied in a transverse direction. Further, a drive force of ½ "$F_D$" is applied to each of the jaws 320a, 320b and the angle "$\alpha_2$" is the angle between the force vector "$F_C$" and the plane normal to the outer surface of each of jaws 320a, 320b at the respective point of contact between cam sleeve 340 and jaws 320a, 320b. As such, the drive force "$F_D$" and the jaw closure force "$F_C$" for jaw assembly 320 an be represented as:

$$F_{C'} = F_{D'} * T_2 \qquad \text{EQ5:}$$

or, in the alternative, as:

$$F_{D'} = \frac{F_{C'}}{T_2} \qquad \text{EQ 6:}$$

where "$T_2$" the force transformation multiplier, is:

$$T_2 = \frac{1}{2\tan\alpha_2} \qquad \text{EQ 7:}$$

Comparing Equations 2 and 3 (EQ 2, EQ 3), above, with Equations 5 and 6 (EQ 5, EQ6), above, it is shown that jaw closure mechanism 150 (FIGS. 4A-5B) provides approximately double the jaw closure force for a given drive force or, in the alternative, requires only half the drive force to achieve a given jaw closure force, as compared to prior art jaw assembly 320 (FIG. 6).

The following table, Table 2, indicates an approximation of the force transformation multiplier "$T_2$" for jaw assembly 320 at various different angles "$\alpha_2$":

Again, as shown via comparison of Tables 1 and 2, above, the ratio of transformation multipliers "$T_1$" and "$T_2$" is approximately 2 over the range of angles.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

What is claimed is:

1. A jaw closure mechanism for use in a surgical clip applier having first and second jaws movable relative to one another between a spaced-apart position and an approximated position to form a surgical clip about tissue, the jaw closure mechanism comprising:
   first and second eccentric wheels rotatably coupled to the respective first and second jaws, each of the first and second eccentric wheels including a center and a pivot point that is offset relative to the center; and
   a continuous cable looped about each of the first and second eccentric wheels, the continuous cable engaged to the first eccentric wheel at a first engagement point and to the second eccentric wheel at a second engagement point such that, upon application of a drive force to the continuous cable, the first and second eccentric wheels are rotated and displaced relative to the respective first and second jaws from a first position to a second position to urge the first and second jaws from the spaced-apart position to the approximated position,
   wherein, in the first position, the center, the pivot point, and the engagement point of each of the first and second eccentric wheels are axially aligned with one another.

2. The jaw closure mechanism according to claim 1, wherein, in the second position, the center, the pivot point, and the engagement point of each of the first and second eccentric wheels are angled with respect to one another.

3. The jaw closure mechanism according to claim 1, further comprising a drive bar coupled to the continuous cable and configured to apply the drive force to the continuous cable.

4. The jaw closure mechanism according to claim 3, wherein the drive bar is selectively translatable between a more distal position and a more proximal position to apply the drive force to the continuous cable.

5. The jaw closure mechanism according to claim 4, wherein, upon translation of the drive bar from the more distal position to the more proximal position, the continuous cable applies an oblique force to each of the first and second eccentric wheels.

6. The jaw closure mechanism according to claim 5, wherein the oblique force applied to each of the first and second eccentric wheels urges the first and second eccentric wheels to displace and rotate relative to the respective first and second jaws, thereby applying a jaw closure force to the first and second jaws to move the first and second jaws from the spaced-apart position to the approximated position.

7. The jaw closure mechanism according to claim 6, wherein the jaw closure force is a product of the drive force and a force transformation multiplier, the force transformation multiplier being inversely proportional to an angle defined between a direction of the oblique force and a direction of the jaw closure force.

8. The jaw closure mechanism according to claim 7, wherein, the rotation and displacement of the first and second eccentric wheels minimizes the angle defined between the direction of the oblique force and the direction of the jaw closure force as the first and second eccentric wheels are transitioned from the first position to the second position, thereby maximizing the force transformation multiplier.

9. The jaw closure mechanism according to claim 1, wherein the jaw closure mechanism is releasably engagable with the first and second jaws.

10. The jaw closure mechanism according to claim 1, further comprising a drive bar coupled to a proximal segment of the continuous cable and configured to apply the drive force to the continuous cable.

11. A surgical clip applier, comprising: a jaw assembly having first and second jaws movable between a spaced-apart position and an approximated position to apply a surgical clip to tissue; and
a jaw closure mechanism, the jaw closure mechanism including:
first and second eccentric wheels rotatably coupled to the respective first and second jaws, each of the first and second eccentric wheels including a center and a pivot point that is offset relative to the center; and
a continuous cable disposed about each of the first and second eccentric wheels, the continuous cable engaged to the first eccentric wheel at a first engagement point and to the second eccentric wheel at a second engagement point such that, upon application of a longitudinal drive force to the continuous cable, the continuous cable applies an oblique force to each of the first and second eccentric wheels to rotate and displace the first and second eccentric wheels relative to the respective first and second jaws, thereby applying a transverse jaw closure force to the first and second jaws to urge the first and second jaws from the spaced-apart position to the approximated position,
wherein, in the spaced-apart position, the center and the pivot point of each of the first and second eccentric wheels are axially aligned with one another.

12. The surgical clip applier according to claim 11, further comprising a drive assembly, the drive assembly including a drive bar that is coupled to the continuous cable, the drive bar selectively translatable between a more distal position and a more proximal position to apply the longitudinal drive force to the continuous cable.

13. The surgical clip applier according to claim 12, further comprising a trigger assembly operably coupled to the drive assembly, the trigger assembly selectively actuatable to translate the drive bar between the more distal position and the more proximal position.

14. The surgical clip applier according to claim 11, wherein the transverse jaw closure force is a product of the longitudinal drive force and a force transformation multiplier, the force transformation multiplier being inversely proportional to an angle defined between a direction of the oblique force and a direction of the transverse jaw closure force.

15. The surgical clip applier according to claim 14, wherein, the rotation and displacement of the first and second eccentric wheels minimizes the angle defined between the direction of the oblique force and the direction of the transverse jaw closure force as the first and second jaws are urged from the spaced-apart position to the approximated position, thereby maximizing the force transformation multiplier.

16. The surgical clip applier according to claim 11, wherein the jaw closure mechanism is releasably engagable with the jaw assembly.

* * * * *